US012747463B2

(12) United States Patent
Speight et al.

(10) Patent No.: US 12,747,463 B2
(45) Date of Patent: Sep. 29, 2026

(54) ENHANCED SOPHOROLIPID DERIVATIVES

(71) Applicant: LOCUS SOLUTIONS IPCO, LLC, Solon, OH (US)

(72) Inventors: Lee Speight, Solon, OH (US); Daniel Hagaman, Mechanicsville, VA (US); Andrew Morris, Richmond, VA (US); Nicholas Callow, Solon, OH (US); Tyler Dixon, Madison, OH (US); Charbel Cherfan, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 312 days.

(21) Appl. No.: 17/776,729

(22) PCT Filed: Feb. 15, 2022

(86) PCT No.: PCT/US2022/016458

§ 371 (c)(1),
(2) Date: Aug. 18, 2022

(87) PCT Pub. No.: WO2022/174190

PCT Pub. Date: Aug. 18, 2022

(65) Prior Publication Data

US 2024/0182940 A1 Jun. 6, 2024

Related U.S. Application Data

(60) Provisional application No. 63/149,477, filed on Feb. 15, 2021.

(51) Int. Cl.

| | |
|---|---|
| ***C12P 19/44*** | (2006.01) |
| ***A01N 43/16*** | (2006.01) |
| ***A01P 1/00*** | (2006.01) |
| ***A61L 2/18*** | (2006.01) |
| ***C07H 15/10*** | (2006.01) |
| ***C11D 3/22*** | (2006.01) |
| ***C11D 3/48*** | (2006.01) |
| *A61L 101/44* | (2006.01) |

(52) U.S. Cl.

CPC .............. *C12P 19/44* (2013.01); *A01N 43/16* (2013.01); *A01P 1/00* (2021.08); *A61L 2/18* (2013.01); *C07H 15/10* (2013.01); *C11D 3/221* (2013.01); *C11D 3/48* (2013.01); *A61L 2101/44* (2020.08)

(58) Field of Classification Search

CPC ......... C12P 19/44; A01N 43/16; C07H 15/10; C07H 1/00; C07H 15/04; C07H 15/26; C11D 3/221; A61L 2101/44; A61L 2202/17; A61L 2101/34; C07K 5/06026; C07K 5/0806; C07K 5/1008

See application file for complete search history.

(56) References Cited

U.S. PATENT DOCUMENTS

| | | | | |
|---|---|---|---|---|
| 2011/0237531 | A1 | 9/2011 | Yanagisawa et al. | |
| 2011/0250153 | A1 | 10/2011 | Owen et al. | |
| 2012/0220464 | A1* | 8/2012 | Giessler-Blank ...... | A01N 43/16 514/777 |
| 2013/0085067 | A1 | 4/2013 | Schofield et al. | |
| 2013/0331466 | A1 | 12/2013 | Gross et al. | |
| 2014/0178444 | A1 | 6/2014 | Stadler et al. | |
| 2016/0280733 | A1 | 9/2016 | Araki et al. | |
| 2017/0143753 | A1 | 5/2017 | Gross et al. | |

FOREIGN PATENT DOCUMENTS

| | | | |
|---|---|---|---|
| CN | 106011108 | A | 10/2016 |
| EP | 1953237 | A1 | 8/2008 |
| EP | 3034613 | A1 | 6/2016 |
| JP | H0426662 | A | 1/1992 |
| JP | H07118284 | A | 5/1995 |
| WO | 2011008570 | A2 | 1/2011 |
| WO | 2011127101 | A1 | 10/2011 |
| WO | 2013003291 | A2 | 1/2013 |
| WO | 2017044953 | A1 | 3/2017 |
| WO | 2014120247 | A1 | 8/2017 |
| WO | 2018049182 | A2 | 3/2018 |
| WO | 2018129299 | A1 | 7/2018 |
| WO | 2018191174 | A1 | 10/2018 |
| WO | 2019133555 | A1 | 7/2019 |
| WO | 2020006194 | A1 | 1/2020 |
| WO | 2021127339 | A1 | 6/2020 |
| WO | 2021173316 | A1 | 9/2021 |
| WO | 2021183526 | A1 | 9/2021 |
| WO | 2021189049 | A1 | 9/2021 |
| WO | 2021236904 | A1 | 11/2021 |

OTHER PUBLICATIONS

Azim, A., et al., "Amino Acid Conjugated Sophorolipids: A New Family of Biologically Active Functionalized Glycolipids." Bioconjugate Chemistry, 2006, 17: 1523-1529.

(Continued)

*Primary Examiner* — Lynn Y Fan

(74) *Attorney, Agent, or Firm* — BENESCH, FRIEDLANDER, COPLAN & ARONOFF LLP

(57) ABSTRACT

Novel sophorolipid derivatives with enhanced antimicrobial activity have been identified as disinfecting active ingredients. These derivatives are produced through a fermentation of *Starmerella bombicola* utilizing dextrose and an oleochemical feedstock that is high in oleic acid. A two-step synthetic scheme is used to generate a reactive aldehyde handle and then install nature-derived cationic biodegradable functional groups. These cationic sophorolipid derivatives are purified using ion exchange resins to afford high purity sophorolipid derivative salts for formulation into disinfecting consumer products.

9 Claims, 15 Drawing Sheets

(56) References Cited

OTHER PUBLICATIONS

Bisht, K.S., et al., "Enzyme-Mediated Regioselective Acylations of Sophorolipids." The Journal of Organic Chemistry, 1999, 64: 780-789.
Carr, J.A., "The Utilization of Enzymes in the Synthesis and Modification of Natural and NonNatural Compounds: A Chemo-Enzymatic Approach to Enantiomerically Pure Compounds." A dissertation submitted in partial fulfillment of the requirements for the degree of doctor of philosophy, Department of chemistry college of arts and sciences, University of South Florida, 2004, pp. 1-212.
Delbeke, E.I.P., et al. "A new class of antimicrobial biosurfactants: quaternary ammonium sophorolipids." Green Chemistry, 2015, 17: 3373-3377.
Wang, H., et al., "Stereocontrolled Syntheses of All Four Stereoisomeric 1,N2-Deoxyguanosine Adducts of the Lipid Peroxidation Product trans-4-Hydroxynonenal." Organic Letters, 2001, 3(22): 3603-3605.
Ahn, C., et al., "Tuning surface-active properties of bio-surfactant sophorolipids by varying fatty-acid chain lengths." Korean Journal of Engineering, 33 (2016): pp. 2127-2133.
Ashby, R. D., et al., "The use of fatty acid esters to enhance free acid sophorolipid synthesis." Biotechnology Letter, 28 (2006): pp. 253-260.
Delbeke, E. I. P., et al., "Chemical and enzymatic modification of sophorolipids." Green Chemistry, 18.1 (2016): pp. 76-104.
Delbeke, E. I. P., et al., "Sophporolipid Amine Oxide Production by a Combination of Fermentation Scale-up and Chemical Modification. " Industrial & Engineering Chemistry Research, 55.27 (2016): pp. 7273-7281.
De Rienzo, M. A. D., et al., "Sophorolipid biosurfactants: Possible uses as antibacterial and antibiofilm agent." New Biotechnology, 32.6 (2015): pp. 720-726.
Koh, A., et al., "Molecular editing of sophorolipids by esterification of lipid moieties: Effects on interfacial properties at paraffin and synthetic crude oil-water interfaces." Colloids and Surfaces A: Physiochemical and Engineering Aspects, 507 (2016): pp. 170-181.
Koh, A., et al., "A versatile family of sophorolipid esters: Engineering surfactant structure for stabilization of lemon oil-water interfaces." Colloids and Surfaces A: Physiochemical and Engineering Aspects, 507 (2016): pp. 152-163.
Li, S., et al., "Biological tailoring of novel sophorolipid molecules an their derivatives." Biofuels, Bioproducts and Biorefining, 15.6 (2021): pp. 1938-1949.
Mandankar, C. S., et al., "Review on sophorolipids—a promising microbial bio-surfactant." Tenside Surfactants Detergents, 60.2 (2023): pp. 95-105.
Peng, Y., et al., "Poly(sophorolipid) Structural Variation: Effects on Biomaterial Physical and Biological Properties." Biomacromolecules, 15.11 (2014): pp. 4214-4227.
Price, N. P. J., et al., "Structural characterization of novel sophorolipid biosurfactants from a newly identified species of Candida yeast." Carbohydrate Reseach, 348 (2012): pp. 33-41.
Rispoli, F. J., et al., "Optimization of the Fermentation Media for Sophorolipid Production from Candida bombicola ATCC 22214 Using a Simplex Centroid Design." Biotechnology Progress, 26.4 (2010): pp. 938-944.
Satpute, S. K., et al., "Multiple Roles of Biosurfactants in Biofilms." Current Pharmaceutical Design, 22.11 (2016): pp. 1429-1448.
Valotteau, C., et al., "Nanoscale antiadhesion properties of sophorolipid-coated surfaces against pathogenic bacteria." Nanoscale Horizons, 4.4 (2019): pp. 975-982.
Vedaraman, N., et al., "The effect of medium composition on the production of sophorolipids and the tensiometric properties by Starmerella bombicola MTCC 1910." Polish Journal of Chemical Technology, 12.2 (2010): pp. 9-13.
You, J., et al., "Hydrolytic metalloenzyme models: Enantioselective hydrolysis of long chain a-amino acid esters by chiral metallomicelles composed of lipophilic I-histidinol." Journal of Molecular Catalysis A: Chemical, 202.1-2 (2003): pp. 17-22.
Zerkowski, J. A., et al., "Head Group-Modified Sophorolipids: Synthesis of New Cationic Zwitterionic, and Anionic Surfactants." Journal of Surfactants and Detergents, 9 (2006): pp. 57-62.

* cited by examiner

SophoRAM

SophoKAM

SophoHAM

SophoG$_n$RAM
n = 1, 2, 3, or 4

SophoG$_n$KAM
n = 1, 2, 3, or 4

SophoG$_n$HAM
n = 1, 2, 3, or 4

$R_1$ = H, Ac
$R_2$ = $CH_2$, $(CH_2)_{10}$
$R_3$ = Me, Et, n-Bu
$R_4$ =

$R_1$ = H, Ac
$R_2$ = $CH_2$, $(CH_2)_{10}$
$R_3$ = Me, Et, n-Bu
$R_4$ =

SophoR2AM

SophoR4AM

SophoR3AM $R_1$ = H, Ac $R_2$ = $CH_2$, $(CH_2)_{10}$ $R_3$ = Me, Et, n-Bu $R_4$ = , , , H $R_5$ = , , $R_1$ = H, Ac $R_2$ = $CH_2$, $(CH_2)_{10}$ $R_3$ = Me, Et, n-Bu $R_4$ = , , , H $R_5$ = , , $R_1$ = H, Ac
$R_2$ = $CH_2$, $(CH_2)_{10}$
$R_3$ = Me, Et, n-Bu $R_1$ = H, Ac
$R_2$ = $CH_2$, $(CH_2)_{10}$
$R_3$ = Me, Et, n-Bu $R_1$ = H, Ac
$R_2$ = $CH_2$, $(CH_2)_{10}$
$R_3$ = Me, Et, n-Bu $R_1$ = H, Ac
$R_2$ = $CH_2$, $(CH_2)_{10}$
$R_3$ = Me, Et, n-Bu 1 2

2

ENHANCED SOPHOROLIPID DERIVATIVES

CROSS-REFERENCE TO RELATED APPLICATION

This application is a National Stage Application of International Application No. PCT/US2022/016458, filed Feb. 15, 2022; which claims the priority benefit of U.S. provisional patent application No. 63/149,477 filed Feb. 15, 2021, both of which are incorporated by reference herein in their entirety.

BACKGROUND OF THE INVENTION

Consumers utilize, and are exposed to, household and personal care products every day. For example, most consumers' daily routine includes the use of make-up, cleansers, oral care products, and/or other personal care and hygiene products. Additionally, cleaning compositions are utilized daily for disinfecting surfaces, as well as removing deposits such as salts in, for example, kitchens and bathrooms. While many of these types of products contain harsh chemicals as active ingredients, additional chemicals may be included as additives that, for example, help with properties such as viscosity, foaming, corrosion prevention, and solubility of fragrances, dyes, and active components.

One specific category of products that utilize particularly harsh chemicals are, disinfecting products. Disinfectants are essential for industry, consumers, and healthcare facilities to reduce the risk of human and animal infection by opportunistic pathogens, combat pandemics, and provide sterility for medical procedures. However, manufacturers and formulators of disinfecting products face significant issues in providing efficacious products that are safe for human exposure and readily biodegrade in the environment. The challenge centers on the fact that the active ingredients in disinfecting products have inherent acute hazards including chemical burns and toxicity, and their broad activity limits their biodegradability. Examples of these disinfecting ingredients include: short chain alcohols (SCAs), hypochlorite salts, peroxides, and quaternary ammonium compounds (QACs).

Toxicity to humans and domestic animals is the short-term problem with existing disinfecting active ingredients. The environmental damage that can be attributed to these ingredients has yet to be fully understood; however, it is largely dose dependent. SCAs, hypochlorite salts, and peroxides have all been shown to biodegrade with rates that do not suggest significant accumulation in the environment. Large spills or deliberate application of these types of disinfecting ingredients do cause environmental disruption, though the effects are not long-lasting.

QACs, on the other hand, have been shown to persist in the environment. While biodegradation pathways have been shown under laboratory aerobic conditions, QACs, especially those containing aromatic scaffolds, are prone to accumulate in environmental sludges and partition poorly to aqueous media. This removes QACs from an aerobic environment in which biodegradation can occur. Accumulation of QACs in anaerobic environmental sludges and soils poses a significant challenge. Typical methods to remove other nitrogen-containing environmental contaminations, both natural and human-activity promoted, are severely limited by the presence of QACs.

QAC biodegradation in anaerobic sludge environments is possible, but the principal breakdown products of QACs include short alkyl amines such as methyl amine. Alkyl amines can accumulate within the microbes capable of degrading QACs, leading to inhibition of QAC degrading enzymes and/or toxicity to the microbes themselves. Further complicating the matter, QACs have been shown to inhibit methanogenesis and other anaerobic digestion pathways used by microbes to degrade other compounds. The risk of QACs in the environment thus entails the risk of accumulation of other hazardous chemicals that would typically degrade.

In addition to the problem of QAC accumulation in the environment and its impacts on microbes essential for biodegradation pathways, recent research has suggested that QAC environmental accumulation is accelerating the development of microbes that are resistant to traditional antibiotics. The same genes found to be responsible for conferring resistance to QACs in bacteria are associated with drug resistant bacteria studied by medical researchers. The mechanism of this resistance involves the use of efflux proteins with broad specificity towards exogenous compounds. Thus, accumulation of QACs in the environment will lead to the selection of bacteria that are capable of resisting them, and, inadvertently, potentially resist traditional antibiotics.

There are a variety of nature-derived molecules that have been shown to have some efficacy as disinfecting active ingredients. The most studied of these types of molecules are antimicrobial peptides (AMPs), or cationic host defense peptides. While the strong performance and compatibility with human and animal health makes AMPs a prime candidate for use as disinfecting active ingredients, contemporary technology is unable to produce them cost effectively. The lack of a method to produce AMPs at costs conducive to commercialization has prevented their use as disinfecting active ingredients and as therapeutics.

Another nature-derived class of molecules that have properties that suggest utility as disinfecting active ingredients are biosurfactants. Biosurfactants are microbially-derived amphiphilic molecules consisting of both hydrophobic (e.g., a fatty acid) and hydrophilic domains (e.g., a sugar). Due to their amphiphilic nature, biosurfactants can partition at the interfaces between different fluid phases such as oil/water or water/air interfaces. Unlike synthetic surfactants, biosurfactants can be effective in hot or cold water, and at either extreme of the pH scale. Additionally, biosurfactants are biodegradable and non-toxic.

Glycolipid biosurfactants, in particular, have many important physiological roles in cellular biology, chiefly as a major component of cell membranes; however, they have gained attention in recent years due to potentially servicing as biological replacements for legacy surfactants. Sophorolipids (SLP) are specific glycolipids of interest. Contrary to AMPs, however, SLP lack sufficient activity on their own to serve as a disinfecting active ingredient.

SLP comprise a sophorose consisting of two glucose molecules, linked to a fatty acid by a glycosidic ether bond. SLP are categorized into two general forms: the lactonic form, where the carboxyl group in the fatty acid side chain and the sophorose moiety form a cyclic ester bond; and the acidic form, or linear form, where the ester bond is hydrolyzed. In addition to these forms, there exists a number of derivatives characterized by the presence or absence of double bonds in the fatty acid side chain, the length of the carbon chain, the position of the glycosidic ether bond, the presence or absence of acetyl groups introduced to the hydroxyl groups of the sugar moiety, and other structural parameters.

Fermentation of yeast cells in a culture substrate including a sugar and/or lipids and fatty acids with carbon chains of differing length can be used to produce a variety of SLP. The yeast *Starmerella* (*Candida*) *bombicola* is one of the most widely recognized producers of SLP. Typically, the yeast produces both lactonic and linear SLP during fermentation, with about 60-70% of the SLP comprising lactonic forms, and the remainder comprising lactonic forms.

Production of SLP using yeast fermentation generally results in a range of molecules with a distribution of structures. Additionally, because of the nature of biological processes, it is difficult to standardize the exact concentration of pure SLP that can be extracted from a yeast culture. Furthermore, crude form SLP can have a cloudy appearance and certain undesirable smell. Thus, purification is often necessary to produce a desirable and marketable product.

Increasingly, consumers are looking for cleaning products, as well as other household and personal care products, that are non-toxic, non-irritating to the skin and/or eyes, and with a reduced impact on the environment, but these safer and more sustainable products are still expected to deliver performance on many attributes, such as cleaning and reduction of germs, at parity to traditional products. Due to the limited set of natural or sustainable materials that meet these needs, formulating safe and environmentally-friendly cleaning compositions remains a challenge.

Thus, there is a need for improved cleaning compositions that are effective for disinfecting materials and/or surfaces and that do not contain harmful or polluting chemicals or synthetically-derived disinfecting agents.

BRIEF SUMMARY OF THE INVENTION

The present application provides materials and methods for producing sophorolipids (SLP) that are amenable to derivatization; materials and methods for derivatizing sophorolipids; materials and methods for purifying sophorolipids to a high level of purity; and derivatized SLP produced according to the described methods. More specifically, in certain embodiments, processes for producing cationic SLP derivatives are provided, wherein in some embodiments, the processes comprise a two-step synthetic scheme to generate a reactive aldehyde handle and then install cationic biodegradable functional groups thereto. The SLP and cationic SLP derivatives can be purified using, for example, ion exchange resins to afford high purity SLP and SLP derivative salts for formulation into, for example, cleaning and disinfecting consumer products.

Advantageously, in certain embodiments, the SLP produced, derivatized and/or purified according to the subject invention exhibit advantageous antimicrobial activity and can be used as disinfecting active ingredients in households, industrial settings, office and retail settings, and in healthcare. Thus, in certain embodiments, the subject invention provides advantageous novel SLP derivatives, including, for example, those described in the Figures and through the subject description.

In preferred embodiments, the subject methods initially comprise producing standardized SLP molecular "substrates" for producing derivatized and/or purified SLP. FIG. 1. In certain embodiments, this entails cultivating a sophorolipid-producing yeast in a submerged fermentation reactor comprising a tailored oleochemical feedstock to produce a yeast culture product, said yeast culture product comprising fermentation broth, yeast cells and crude SLP having a mixture of two or more molecular structures.

In certain embodiments, the sophorolipid-producing yeast is *Starmerella bombicola*, or another member of the *Starmerella* and/or *Candida* clades. For example, *S. bombicola* strain ATCC 22214 can be used according to the subject methods.

The mixture of molecular structures can comprise, for example, lactonic SLP, linear SLP, de-acetylated SLP, mono-acetylated SLP, di-acetylated SLP, esterified SLP, SLP with varying hydrophobic chain lengths, SLP with fatty acid-amino acid complexes attached, and others, including those that are and/or are not specifically exemplified within this disclosure.

In certain embodiments, the distribution of the mixture of SLP molecules can be altered by adjusting fermentation parameters, such as, for example, feedstock, fermentation time, and/or dissolved oxygen levels.

In preferred embodiments, the oleochemical feedstock is tailored to include a source of oleic acid. In certain embodiments, the oleic acid content is high, e.g., at least 75%, at least 80%, at least 85%, at least 90%, at least 95%, or at least 99%. In some embodiments, the oleochemical feedstock comprises oleic acid sources exclusively.

Advantageously, in certain embodiments, use of high-oleic acid and/or exclusively-oleic acid oleochemical feedstock results in a yeast culture product comprising less diversity of SLP molecular structures than with feedstocks containing sources of other fatty acids, wherein the principal SLP molecules produced contain an C18 carbon chain and a single unsaturated bond at the ninth carbon.

In certain embodiments, in order to ensure complete consumption of the oleochemical feedstock by the yeast, fermentation time is extended past what is typical for producing SLP. In some embodiments, the fermentation time is within a range of 40 hours to 150 hours, or 50 to 120 hours.

In certain embodiments, the dissolved oxygen (DO) levels are controlled during fermentation to narrow the structural diversity of SLP molecules produced in the yeast culture product. Preferably, the DO levels are maintained at high levels such that, for example, oxygen transfer occurs at a rate of above 50 mM per liter per hour, above 60 mM per liter per hour, or above 70 mM per liter per hour.

In certain embodiments, production of the SLP molecular "substrate" further comprise post-fermentation alteration of the crude SLP molecules produced in the yeast culture product. In one embodiment, the crude SLP are hydrolyzed to produce linear SLP. In some embodiments, the linear SLP are de-acetylated.

Hydrolysis preferably comprises mixing the crude SLP with a pH-raising base, such as, e.g., sodium hydroxide, potassium hydroxide, and/or ammonium hydroxide, wherein the increased pH results in breakage of the lactone bond in lactonic SLP and conversion thereof to linear SLP (FIG. 2), as well as, in some embodiments, de-acetylation of mono- and/or di-acetylated SLP.

In some embodiments, when spectator cations are present in the hydrolysis process, the crude linear SLP are purified using ion exchange resins. More specifically, in preferred embodiments, the crude linear sophorolipids are circulated through an ion exchange bed using, for example, a peristaltic pump or other type of pump, containing ion exchange sites for a period of time, e.g., 15 minutes to 20 hours, 3 hours to 15 hours, 4 hours to 12 hours, or preferably, 30 minutes to 3 hours.

In certain embodiments, the amount of ion exchange sites is equimolar or up to 1.5 molar or more to the concentration of hydroxide salts utilized in the hydrolysis reaction. In some embodiments, the ion exchange sites are cationic exchange sites.

Advantageously, the ion exchange resins provide novel methods for purifying SLP molecules, and for neutralizing the pH of the reaction product without the need for standard quenching methods, which can dilute and/or change the chemistry of an end product.

In preferred embodiments, the linear SLP, having spectator cations removed, serve as the standardized substrates for one or more derivatization and/or purification procedures.

After removal of spectator cations, a two-step synthetic scheme can be employed to generate a reactive aldehyde handle on the linear SLP and then install cationic biodegradable functional groups. FIG. 3.

In preferred embodiments, step one comprises employing ozonolysis to oxidize the olefin moiety of the linear SLP molecule to an ozonide, a reactive 5-membered ring, followed by reducing the resulting SLP-ozonide to produce a linear SLP with an aldehyde handle. FIG. 4. Sophorolipids containing an unsaturated bond at a specific position (e.g., at the ninth carbon of the fatty acid moiety) allows for site-directed functionalization of the sophorolipid molecule.

In some embodiments, step one comprises another route to produce a linear SLP with an aldehyde functional group, wherein the other route involves oxidative cleavage of the unsaturated bond present in the fatty acid tail of the SLP molecule. In certain embodiments, the oxidative cleavage route involves a one-pot, two-stage transformation that can be accomplished via many different chemical reagents to those familiar with the art. In one embodiment, the double bond is first oxidized with osmium tetraoxide ($OsO_4$) in a suitable solvent, which transforms the double bond to a vicinal diol. The vicinal diol can then be cleaved with several different reagents including, but not limited to, compounds such as (Diacetoxyiodo)benzene ($PhI(OAc)_2$), sodium periodate ($NaIO_4$), periodic acid ($HIO_4$), and 2-Iodoxybenzoic acid (IBX).

In certain embodiments, the reactive aldehyde handle, whether produced via ozonolysis or oxidative cleavage, is then used as the site for addition of a primary amine via step two, reductive amination. In certain embodiments, the reductive amination comprises introducing a primary amine to the SLP-aldehyde under reducing conditions. This produces a stable secondary amine that serves as a covalent linkage between the SLP "scaffold" and the "cargo" of the primary amine. FIG. 5.

In certain embodiments, rather than installing an aldehyde handle, the linear SLP substrate can be installed with an amide comprising cationic amino acid functional groups using amide coupling to produce a long-chain amide derivative (e.g., C18). FIG. 6.

In some embodiments, the linear SLP substrate can be installed with an amide to produce a short-chain amide derivative (e.g., C9) by first, truncating the fatty acid moiety via oxidative cleavage, and second, coupling the truncated acid with an amide comprising cationic amino acid functional groups. FIGS. 7A-7B.

Coupling agents for use in amide installation according to the subject invention can include, for example, 1-Ethyl-3-(3-dimethylaminopropyl)carbodiimide (EDCI/HOBt), Benzotriazol-1-yloxytripyrrolidinophosphonium hexafluorophosphate (PYBOP), 2-(1H-Benotriazole-1-yl)-1,1,3,3-tetramethylaminium tetrafluoroborate (TBTU), and/or N,N'-Dicyclohexylcarbodiimide/1-Hydroxybenzotriazole (DCC/HOBt).

In certain embodiments, the linear SLP comprising the aldehyde handle can be converted into a long-chain or short-chain amide utilizing similar reaction schemes. In some embodiments, the truncated acid (FIG. 7A) can serve as an alternative substrate for installing the aldehyde handle.

In certain embodiments, the primary amine according to the subject methods is a cationic amino acid, such as, e.g., arginine, lysine or histidine. In certain embodiments, the primary amine is a short peptide containing repeats of cationic amino acids. In certain embodiments, the primary amine is a short peptide containing glycine residues as spacers, either between the SLP scaffold and the primary amine cargo, or between cationic amino acid residues. FIG. 8.

In certain embodiments, the unique cationic nature of the SLP derivatives of the subject invention allows for cationic ion exchange resins to be used for selective purification. Application of a crude reaction mixture from the aforementioned processes to cationic ion exchange resin allows for the selective retention of cationic species and for the selective removal of unreacted SLP and/or SLP that did not contain the desired chain length or character (e.g., C18, monounsaturated).

In preferred embodiments, removal of the SLP cationic derivatives from the resin is accomplished by application of an electrolyte solution containing a large concentration of monovalent metallic cations. The monovalent metallic cations in large concentration outcompete the bound SLP cationic derivatives, allowing for them to exchange on the resin and produce a highly purified stream of SLP cationic derivatives. FIGS. 8-12.

In certain embodiments, the derivatized cationic SLP produced according to the subject methods can be used as active ingredients in environmentally-friendly cleaning compositions for efficiently disinfecting and/or sanitizing materials and/or surfaces contaminated with, for example, bacteria, viruses, fungi, molds, mildew, protozoa, biofilms, and/or other infectious organisms. Advantageously, in preferred embodiments, the compositions and methods are at least as effective for disinfecting materials and/or surfaces as antimicrobial peptides (AMPs), or cationic host defense peptides, as well as other chemical and/or synthetic cleaning formulations, such as QACs and SCAs.

Optionally, the cleaning composition can further comprise one or more other components, including, for example, carriers (e.g., water), hydrophilic and/or hydrophobic syndetics, sequestrants, builders, solvents, organic and/or inorganic acids (e.g., lactic acid, citric acid, boric acid), essential oils, botanical extracts, cross-linking agents, chelators, fatty acids, alcohols, pH adjusting agents, reducing agents, calcium salts, carbonate salts, buffers, enzymes, dyes, colorants, fragrances, preservatives, terpenes, sesquiterpenoids, terpenoids, emulsifiers, demulsifiers, foaming agents, defoamers, bleaching agents, polymers, thickeners and/or viscosifiers.

The cleaning compositions can be formulated as, for example, microemulsions, dissolvable powders and/or granules, pressed powders, loose powders, solid bars, diluted sprays, concentrates, aerosols, foams, toilet bowl cleaners, laundry detergents, dishwashing detergents, encapsulated dissolvable pods, gels, and/or as a pre-moistened or water-activated cloth, sponge, wipe or other substrate.

In preferred embodiments, the subject invention provides methods for disinfecting and/or sanitizing materials and/or surfaces having a deleterious microorganism therein or thereon, wherein the method comprises applying a cleaning composition of the subject invention to the material and/or surface such that the composition is contacted with the deleterious microorganism. Advantageously, the methods are safe for use in household, commercial, healthcare and industrial settings and in the presence of humans, plants and animals.

The cleaning composition can be applied to, for example, counters, floors, toilets, clothing and textiles, medical devices and implants, plastic and ceramic dishes, carpets and rugs, toys, doorknobs, bathtubs, sinks, glass, and windows. The composition can also be used to disinfect fluids, such as air and/or water.

Advantageously, the present invention can be used without causing harm to users and without releasing large quantities of polluting and toxic compounds into the environment. Additionally, the compositions and methods utilize components that are biodegradable and toxicologically safe. Thus, the present invention can be used in a variety of industries as a "green" disinfectant.

DETAILED DESCRIPTION

Figure 1:
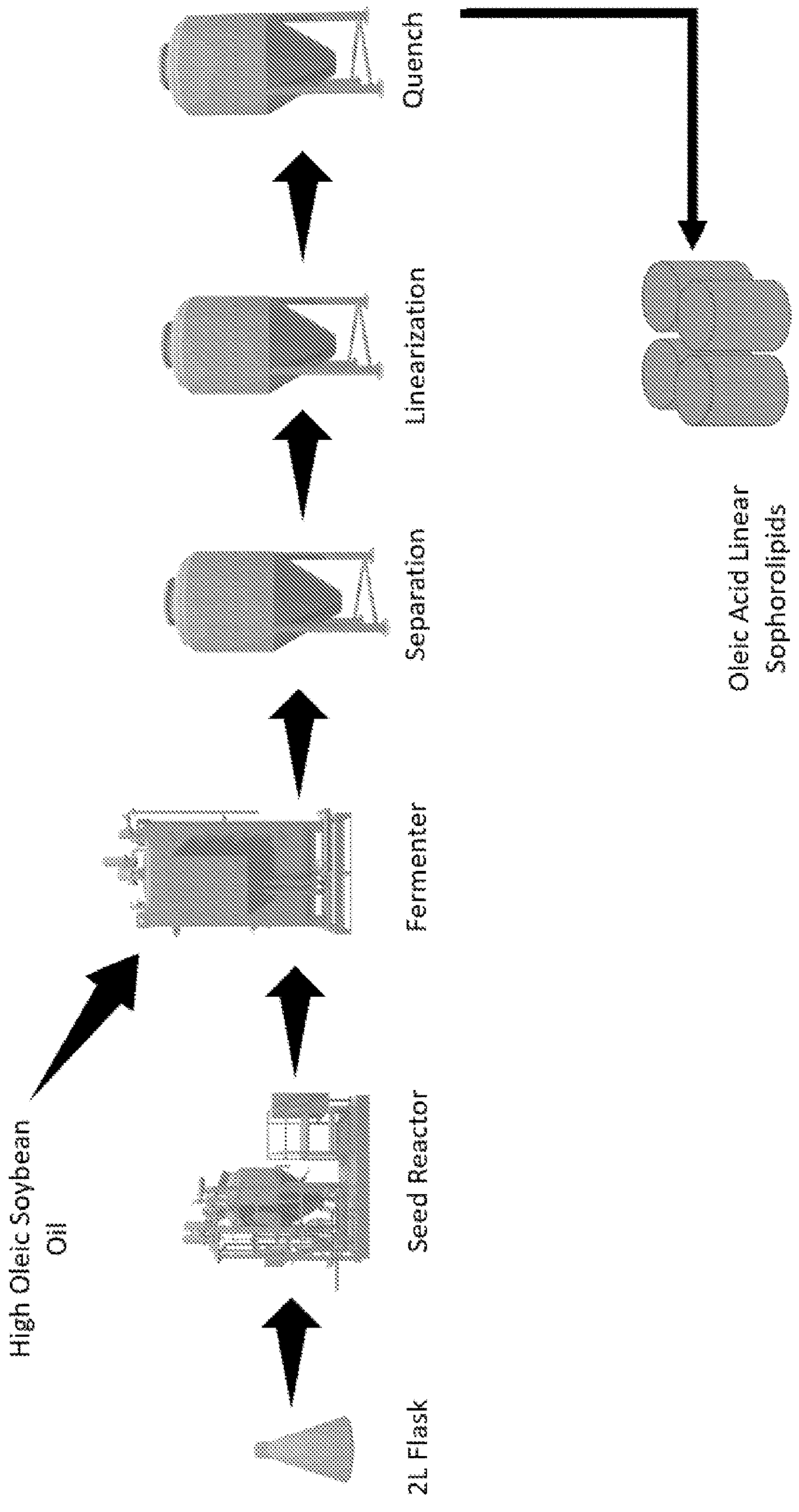
FIG. 1 depicts a production scheme according to an embodiment of the subject invention used to produce linear sophorolipids containing an oleic acid chain.

The present application provides materials and methods for producing sophorolipids (SLP) that are amenable to derivatization; materials and methods for derivatizing sophorolipids; materials and methods for purifying sophorolipids to a high level of purity; and derivatized SLP produced according to the present methods.

In certain embodiments, the subject invention provides cationic SLP derivative molecules, including, for example, those that are described in the Figures and throughout the subject Description. These cationic SLP derivatives can be purified using, for example, ion exchange resins to afford high purity SLP derivative salts for formulation into disinfecting consumer products Sophorolipids are glycolipid biosurfactants produced by, for example, various yeasts of the *Starmerella* clade. SLP consist of a disaccharide sophorose linked to long-chain hydroxy fatty acids. They can comprise a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid can have, for example, 11 to 20 carbon atoms, and may contain one or more unsaturated bonds. Furthermore, the sophorose residue can be acetylated on the 6- and/or 6'-position(s). The fatty acid carboxyl group can be free (acidic or linear form) or internally esterified at the 4"-position (lactonic form). In most cases, fermentation of SLP results in a mixture of hydrophobic (water-insoluble) SLP, including, e.g., lactonic SLP, mono-acetylated linear SLP and di-acetylated linear SLP, and hydrophilic (water-soluble) SLP, including, e.g., non-acetylated linear SLP.

As used herein, the term "sophorolipid," "sophorolipid molecule," "SLP" or "SLP molecule" includes all forms, and isomers thereof, of SLP molecules, including, for example, acidic (linear) SLP and lactonic SLP. Further included are mono-acetylated SLP, di-acetylated SLP, esterified SLP, SLP with varying hydrophobic chain lengths, SLP with fatty acid-amino acid complexes attached, and other, including those that are and/or are not described within in this disclosure.

In some embodiments, the SLP molecules according to the subject invention are represented by General Formula (1) and/or General Formula (2), and are obtained as a collection of 30 or more types of structural homologues having different fatty acid chain lengths ($R^3$), and, in some instances, having an acetylation or protonation at $R^1$ and/or $R^2$.

(1)

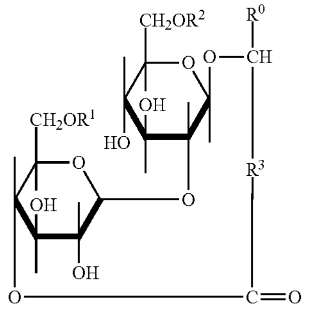

(2)

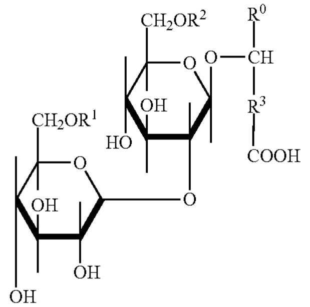

In General Formula (1) or (2), $R^0$ can be either a hydrogen atom or a methyl group. $R^1$ and $R^2$ are each independently a hydrogen atom or an acetyl group. $R^3$ is a saturated aliphatic hydrocarbon chain, or an unsaturated aliphatic hydrocarbon chain having at least one double bond, and may have one or more Substituents.

Non-limiting examples of the Substituents include halogen atoms, hydroxyl, lower (C1-6) alkyl groups, halo lower (C1-6) alkyl groups, hydroxy lower (C1-6) alkyl groups, halo lower (C1-6) alkoxy groups, and others. $R^3$ typically has up to 20 carbon atoms. In preferred embodiments of the subject invention, the fatty acid moiety has 9 or 18 carbon atoms.

Selected Definitions

As used herein, a "green" compound or material means at least 95% derived from natural, biological and/or renewable sources, such as plants, animals, minerals and/or microorganisms, and furthermore, the compound or material is biodegradable. Additionally, in some embodiments, "green" compounds or materials are minimally toxic to humans and can have a LD50>5000 mg/kg. A "green" product preferably does not contain any of the following: non-plant based ethoxylated surfactants, linear alkylbenzene sulfonates (LAS), ether sulfates surfactants or nonylphenol ethoxylate (NPE). In certain preferred embodiments, the SLP molecules, including the derivatized SLP molecules, described herein are "green" compounds with minimal toxicity to users.

As used herein, a "biofilm" is a complex aggregate of microorganisms, such as bacteria, yeast, or fungi, wherein the cells adhere to each other and/or to a surface using an extracellular matrix. The cells in biofilms are physiologically distinct from planktonic cells of the same organism, which are single cells that can float or swim in liquid medium.

As used herein, "contaminant" refers to any substance that causes another substance or object to become fouled or impure. Contaminants can be living or non-living and can be inorganic or organic substances or deposits. Furthermore, contaminants can include, but are not limited to, hydrocarbons, such as petroleum or asphaltenes; fats, oils and greases (FOG), such as cooking grease, plant-based oils, and lard; lipids; waxes, such as paraffin; resins; microorganisms, such as bacteria, biofilms, viruses, fungi, molds, mildews, protozoa, parasites or another infectious microorganisms; stains; or any other substances referred to as, for example, dirt, dust, scale, sludge, crud, slag, grime, scum, plaque, buildup, or residue.

As used herein, "fouling" means the accumulation or deposition of contaminants on a surface of, for example, a piece of equipment in such a way as to compromise the structural and/or functional integrity of the equipment. Fouling can cause clogging, plugging, deterioration, corrosion, and other problems associated therewith, and can occur on both metallic and non-metallic materials and/or surfaces. Fouling that occurs as a result of living organisms, for example, biofilms, is referred to as "biofouling."

As used herein, "cleaning" as used in the context of contaminants or fouling means removal or reduction of contaminants from a material and/or surface.

As used herein, to "disinfect" means to control or substantially control a deleterious microorganism in 10 minutes or less, preferably in 5 minutes or less, more preferably in 2 minutes or less, after the time of contact between the composition and the deleterious microorganism (i.e., exposure time).

As used herein, "control" in the context of a microorganism means killing, immobilizing, destroying, removing, reducing population numbers of, and/or otherwise rendering the microorganism incapable of reproducing and/or causing substantial harm or fouling.

In preferred embodiments, the deleterious microorganisms are "substantially controlled," meaning at least 90%, preferably at least 95%, or more preferably, at least 99% of the microorganism's population within a specified area is controlled.

In certain preferred embodiments, 100% of the deleterious microorganism is controlled, meaning the surface and/or material has been "sanitized."

As used herein, a "deleterious" or "pathogenic" microorganism refers to any single-celled or acellular organism that is capable of causing an infection, disease or other form of harm in another organism. As used herein, deleterious or pathogenic microorganisms are infectious agents and can include, for example, bacteria, cyanobacteria, biofilms, viruses, virions, viroids, fungi, molds, mildews, protozoa, prions, and algae. In certain embodiments, a deleterious microorganism can include multicellular organisms, such as, for example, certain parasites, helminths, nematodes and/or lichens.

As used herein, "preventing" situation or occurrence refers to avoiding, delaying, forestalling, or minimizing the onset of a particular sign or symptom of situation or occurrence. Prevention can, but is not required to be, absolute or complete, meaning the situation or occurrence may still develop at a later time. Prevention can include reducing the severity of the onset of situation or occurrence, and/or inhibiting the progression of the situation or occurrence to one that is more severe.

As used herein, "surfactant" refers to a substance or compound that reduces surface tension when dissolved in water or water solutions, or that reduces interfacial tension between two liquids, or between a liquid and a solid. The term "surfactant" thus includes cationic, anionic, nonionic, zwitterionic, amphoteric agents and/or combinations thereof. By "biosurfactant" is meant a surfactant produced by a living cell and/or using naturally-derived sources.

As used herein, "base surfactant" refers to a surfactant or amphiphilic molecule that exhibits a strong tendency to adsorb at interfaces in a relatively ordered fashion, oriented perpendicular to the interface.

As used herein, the term "syndetic" (meaning to join or link together, as in mixing water and oil) refers to a relatively weak amphiphile that exhibits a significant ability to adsorb at an oil-water interface (from either the water phase, hence a "hydrophilic syndetic," or from the oil phase, hence a "hydrophobic syndetic") only when the interface already bears an adsorbed layer of a base surfactant or mixture of base surfactants. Adsorption of syndetics at oil-water interfaces is thought to affect the spacing and/or the order of the adsorbed ordinary surfactants in a manner that is highly beneficial to the production of very low oil-water interfacial tensions, which in turn increases the solubilization of oils and/or the removal of oils from solid materials and/or surfaces.

As used herein, an "isolated" or "purified" nucleic acid molecule, polynucleotide, polypeptide, protein or organic compound, such as a small molecule, is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of other molecules, or the amino acids that flank it, in its naturally-occurring state. An "isolated" strain means that the strain is removed from the environment in which it exists in nature. Thus, the isolated strain may exist as, for example, a biologically pure culture, or as spores (or other forms of the strain).

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19 and 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduces" means a negative alteration, and "increases" means a positive alteration, wherein the alteration is at least 0.001%, 0.01%, 0.1%, 1%, 5%, 10%, 15%, 20%, 25%, 30%, 35%, 45%, 50%, 55%, 60%, 65%, 70%, 75%, 80%, 85%, 90%, 95%, 99%, or 100%, inclusive of all values therebetween.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. All references cited herein are hereby incorporated by reference.

Production and Derivatization of Sophorolipids

The subject invention provides materials and methods for producing, derivatizing and purifying sophorolipids (SLP). Advantageously, the subject invention is suitable for industrial scale production of purified SLP derivatives and uses safe and environmentally-friendly, or "green," materials and processes.

In certain embodiments, the subject invention provides cationic SLP derivative molecules, including those that are described in the Figures and throughout the subject Description. In certain embodiments, the cationic SLP derivative molecules are produced according to the methods described herein.

Production of Standardized SLP Molecular "Substrates"

In preferred embodiments, the subject methods initially comprise producing standardized SLP molecular "substrates" for producing derivatized and/or purified SLP. FIG. 1. In certain embodiments, this entails cultivating a sophorolipid-producing yeast in a submerged fermentation reactor comprising a tailored oleochemical feedstock to produce a yeast culture product, said yeast culture product comprising fermentation broth, yeast cells and SLP having a mixture of two or more molecular structures.

The mixture of molecular structures can comprise, for example, lactonic SLP, linear SLP, de-acetylated SLP, mono-acetylated SLP, di-acetylated SLP, esterified SLP, SLP with varying hydrophobic chain lengths, SLP with fatty acid-amino acid complexes attached, and others, including those that are and/or are not described within in this disclosure.

In certain embodiments, the distribution of the mixture of SLP molecules can be altered by adjusting fermentation parameters, such as, for example, feedstock, fermentation time, and dissolved oxygen levels.

As used herein "fermentation" refers to growth or cultivation of cells under controlled conditions. The growth could be aerobic or anaerobic. Unless the context requires otherwise, the phrase is intended to encompass both the growth phase and product biosynthesis phase of the process.

As used herein, a "broth," "culture broth," or "fermentation broth" refers to a culture medium comprising at least nutrients. If the broth is referred to after a fermentation process, the broth may comprise microbial growth byproducts and/or microbial cells as well.

The microbe growth vessel used according to the subject invention can be any fermenter or cultivation reactor for industrial use. As used herein, the term "reactor," "bioreactor," "fermentation reactor" or "fermentation vessel" includes a fermentation device consisting of one or more vessels and/or towers or piping arrangements. Examples of such reactor includes, but are not limited to, the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments, the bioreactor may comprise a first growth reactor and a second fermentation reactor. As such, when referring to the addition of substrate to the bioreactor or fermentation reaction, it should be understood to include addition to either or both of these reactors where appropriate.

In one embodiment, the fermentation reactor may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, samples may be taken from the vessel for enumeration, purity measurements, SLP concentration, and/or visible oil level monitoring. For example, in one embodiment, sampling can occur every 24 hours.

The microbial inoculant according to the subject methods preferably comprises cells and/or propagules of the desired microorganism, which can be prepared using any known fermentation method. The inoculant can be pre-mixed with water and/or a liquid growth medium, if desired.

The microorganisms utilized according to the subject invention may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is a yeast or fungus. Examples of yeast and fungus species suitable for use according to the current invention, include, but are not limited to *Starmerella* spp. yeasts and/or *Candida* spp. yeasts, e.g., *Starmerella* (*Candida*) *bombicola, Candida apicola, Candida batistae, Candida floricola, Candida riodocensis, Candida stellate* and/or *Candida kuoi*. In a specific embodiment, the microorganism is *Starmerella bombicola*, e.g., strain ATCC 22214.

In certain embodiments, the cultivation method utilizes submerged fermentation in a liquid growth medium comprising a tailored oleochemical feedstock.

In one embodiment, the liquid growth medium comprises one or more sources of carbon. The carbon source can be a carbohydrate, such as glucose, dextrose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as canola oil, madhuca oil, soybean oil, rice bran oil, olive oil, corn oil, sunflower oil, sesame oil, and/or linseed oil; powdered molasses, etc. These carbon sources may be used independently or in a combination of two or more.

In preferred embodiments, the fermentation medium comprises dextrose. In another preferred embodiment, the oleochemical feedstock is tailored to include a source of oleic acid. In certain embodiments, the oleic acid content is high, e.g., at least 75%, at least 80%, at least 85%, at least 90%, at least 95%, or at least 99%. In some embodiments, the oleochemical feedstock comprises oleic acid sources exclusively.

Examples of oleic acid sources include, but are not limited to, high oleic soybean oil, high oleic sunflower oil, high oleic canola oil, olive oil, pecan oil, peanut oil, macadamia oil, grapeseed oil, sesame oil, poppyseed oil, pure oleic acid, madhuca oil, oleic acid alkyl esters, and/or triglycerides of oleic acid. In preferred embodiments, high oleic soybean oil, pure oleic acid, and/or oleic acid alkyl esters are used.

Advantageously, in certain embodiments, use of high-oleic acid and/or exclusively-oleic acid oleochemical feedstock results in a yeast culture product comprising a narrower diversity of SLP molecular structures than with feedstocks containing sources of other fatty acids, wherein the principal SLP molecules produced contain a C18 carbon chain and a single unsaturated bond at the ninth carbon. For example, in certain embodiments, greater than 50% of the SLP molecules contain an C18 carbon chain, preferably greater than 70%, more preferably greater than 85%.

In one embodiment, the liquid growth medium comprises a nitrogen source. The nitrogen source can be, for example, yeast extract, potassium nitrate, ammonium nitrate, ammonium sulfate, ammonium phosphate, ammonia, urea, and/or ammonium chloride. These nitrogen sources may be used independently or in a combination of two or more.

In one embodiment, one or more inorganic salts may also be included in the liquid growth medium. Inorganic salts can include, for example, potassium dihydrogen phosphate, monopotassium phosphate, dipotassium hydrogen phosphate, disodium hydrogen phosphate, potassium chloride, magnesium sulfate, magnesium chloride, iron sulfate, iron chloride, manganese sulfate, manganese chloride, zinc sulfate, lead chloride, copper sulfate, calcium chloride, calcium carbonate, calcium nitrate, magnesium sulfate, sodium phosphate, sodium chloride, and/or sodium carbonate. These inorganic salts may be used independently or in a combination of two or more.

In one embodiment, growth factors and trace nutrients for microorganisms are included in the medium. Inorganic nutrients, including trace elements such as iron, zinc, copper, manganese, molybdenum and/or cobalt may also be included in the medium. Furthermore, sources of vitamins, essential amino acids, proteins and microelements can be included, for example, corn flour, peptone, yeast extract, potato extract, beef extract, soybean extract, banana peel extract, and the like, or in purified forms. Amino acids such as, for example, those useful for biosynthesis of proteins, can also be included.

The method of cultivation can further provide oxygenation to the growing culture. One embodiment utilizes slow motion of air to remove low oxygen-containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

In certain embodiments, the dissolved oxygen (DO) levels are controlled during fermentation to narrow the structural diversity of SLP molecules produced in the yeast culture product. Preferably, the DO levels are maintained at high levels such that, for example, oxygen transfer occurs at a rate at or above 50 mM, at or above 55 mM, at or above 60 mM, at or above 65 mM, or at or above 70 mM per liter per hour.

In some embodiments, the method for cultivation may further comprise adding additional acids and/or antimicrobials in the liquid medium before and/or during the cultivation process. Antimicrobial agents or antibiotics (e.g., streptomycin, oxytetracycline) are used for protecting the culture against contamination. In some embodiments, however, the metabolites produced by the yeast culture provide sufficient antimicrobial effects to prevent contamination of the culture.

In one embodiment, prior to inoculation of the reactor, the components of the liquid culture medium can optionally be sterilized. In one embodiment, sterilization of the liquid growth medium can be achieved by placing the components of the liquid culture medium in water at a temperature of about 85-100° C. In one embodiment, sterilization can be achieved by dissolving the components in 1 to 3% hydrogen peroxide in a ratio of 1:3 (w/v).

In one embodiment, the equipment used for cultivation is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Gaskets, openings, tubing and other equipment parts can be sprayed with, for example, isopropyl alcohol. Air can be sterilized by methods know in the art. For example, the ambient air can pass through at least one filter before being introduced into the vessel. In other embodiments, the medium may be pasteurized or, optionally, no heat at all added, where the use of pH and/or low water activity may be exploited to control unwanted microbial growth.

The pH of the culture should be suitable for the microorganism of interest. In some embodiments, the pH is about 2.0 to about 7.0, about 3.0 to about 5.5, about 3.25 to about 4.0, or about 3.5. Buffers, and pH regulators, such as carbonates and phosphates, may be used to stabilize pH near a preferred value. In certain embodiments, a base solution is used to adjust the pH of the culture to a favorable level, for example, a 15% to 30%, or a 20% to 25% NaOH solution. The base solution can be included in the growth medium and/or it can be fed into the fermentation reactor during cultivation to adjust the pH as needed.

In one embodiment, the method of cultivation is carried out at about 5° to about 100° C., about 15° to about 60° C., about 20° to about 45° C., about 22° to about 35° C., or about 240 to about 28° C. In one embodiment, the cultivation may be carried out continuously at a constant temperature. In another embodiment, the cultivation may be subject to changing temperatures.

According to the subject methods, the microorganisms can be cultivated in the fermentation system for a time period sufficient to achieve a desired effect, e.g., production of a desired amount of cell biomass or a desired amount of SLP. The microbial growth by-product(s) produced by microorganisms may be retained in the microorganisms and/or secreted into the growth medium. The biomass content may be, for example from 5 g/l to 180 g/I or more, from 10 g/l to 150 g/l, or from 20 g/l to 100 g/l.

In certain embodiments, fermentation of the yeast culture occurs for about 40 to 150 hours, or about 48 to 140 hours, or about 72 to 130 hours or about 96 to 120 hours. In certain specific embodiments, fermentation time ranges from 48 to 72 hours, or from 96 to 120 hours.

In some embodiments, the fermentation cycle is ended once the dextrose and/or oleic acid concentrations in the medium are exhausted (e.g., at a level of 0% to 0.5%). In some embodiments, the end of the fermentation cycle is determined to be a time point when the microorganisms have begun to consume trace amounts of SLP.

In certain embodiments, production of the SLP molecular "substrate" further comprises post-fermentation alteration of the SLP molecules produced in the yeast culture product. In one embodiment, this crude SLP composition is hydrolyzed to produce linear SLP. In some embodiments, the linear SLP are de-acetylated. In some embodiments, the linear SLP are peracetylated.

In some embodiments, the method comprises subjecting the crude SLP to alkaline hydrolysis. For example, in one embodiment, the crude SLP can be mixed with equimolar to 1.5 molar concentrations of a base solution, such as, for example, a solution of sodium hydroxide, potassium hydroxide, and/or ammonium hydroxide, to adjust the pH to, e.g., about 4 to 11, about 5 to 11, about 6 to 12, or preferably, about 7 to 9. In certain embodiments, this is achieved by treating the crude SLP with the hydroxide salt solution for 2 to 24 hours, 3 to 20 hours, or 4 to 16 hours at an elevated temperature of, e.g., 75 to 100° C., 80 to 95° C., or 85 to 90° C.

Figure 2:
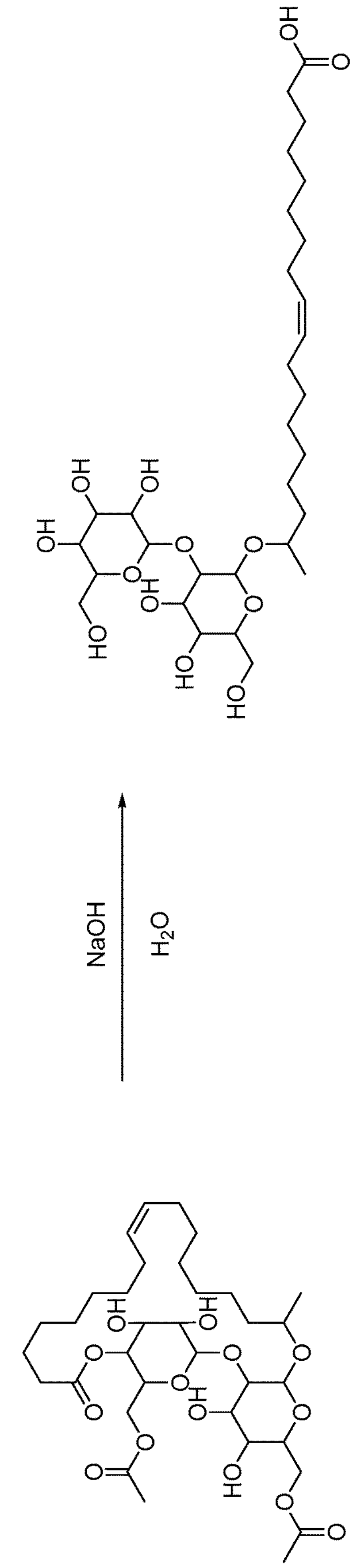
FIG. 2 depicts a reaction scheme according to an embodiment of the subject invention showing hydrolysis of a di-acetylated lactonic sophorolipid to produce a linear sophorolipid.

According to the subject methods, the hydrolysis process results in breakage of the lactone bond of lactonic SLP and conversion thereof to a crude linear SLP. FIG. 2. In certain embodiments, a portion of the crude linear SLP are acetylated, di-acetylated, or peracetylated, wherein the portion comprises from, for example, 1% to 100%, 5% to 75%, or 10 to 50% of the total amount of SLP molecules. In another embodiment, a mono- or di-acetylated SLP molecule can be de-acetylated via the same alkaline hydrolysis process.

In some embodiments, when spectator cations are or may be present in the hydrolysis process, the crude linear SLP are purified using cation exchange resins. More specifically, in preferred embodiments, the crude linear sophorolipids are circulated through an ion exchange bed containing cation exchange sites using, for example, a peristaltic pump or other type of pump, for a period of time from, e.g., 15 minutes to 20 hours, 3 hours to 15 hours, 4 hours to 12 hours, or preferably, 30 minutes to 3 hours.

The amount of cation exchange sites can be, for example, equimolar to 1.5 molar the concentration of hydroxide salts used for the alkaline hydrolysis.

Advantageously, the ion exchange resins provide novel methods for purifying SLP molecules, as well as novel methods for neutralizing the pH of a reaction product without the need for standard quenching methods, which can dilute and/or change the chemical make-up of an end product.

In preferred embodiments, the linear SLP, having spectator cations removed, serve as the standardized substrates for one or more derivatization and/or purification reactions.

Two-Step Generation of Cationic SLP Derivatives Via Aldehyde Handle

Figure 3:
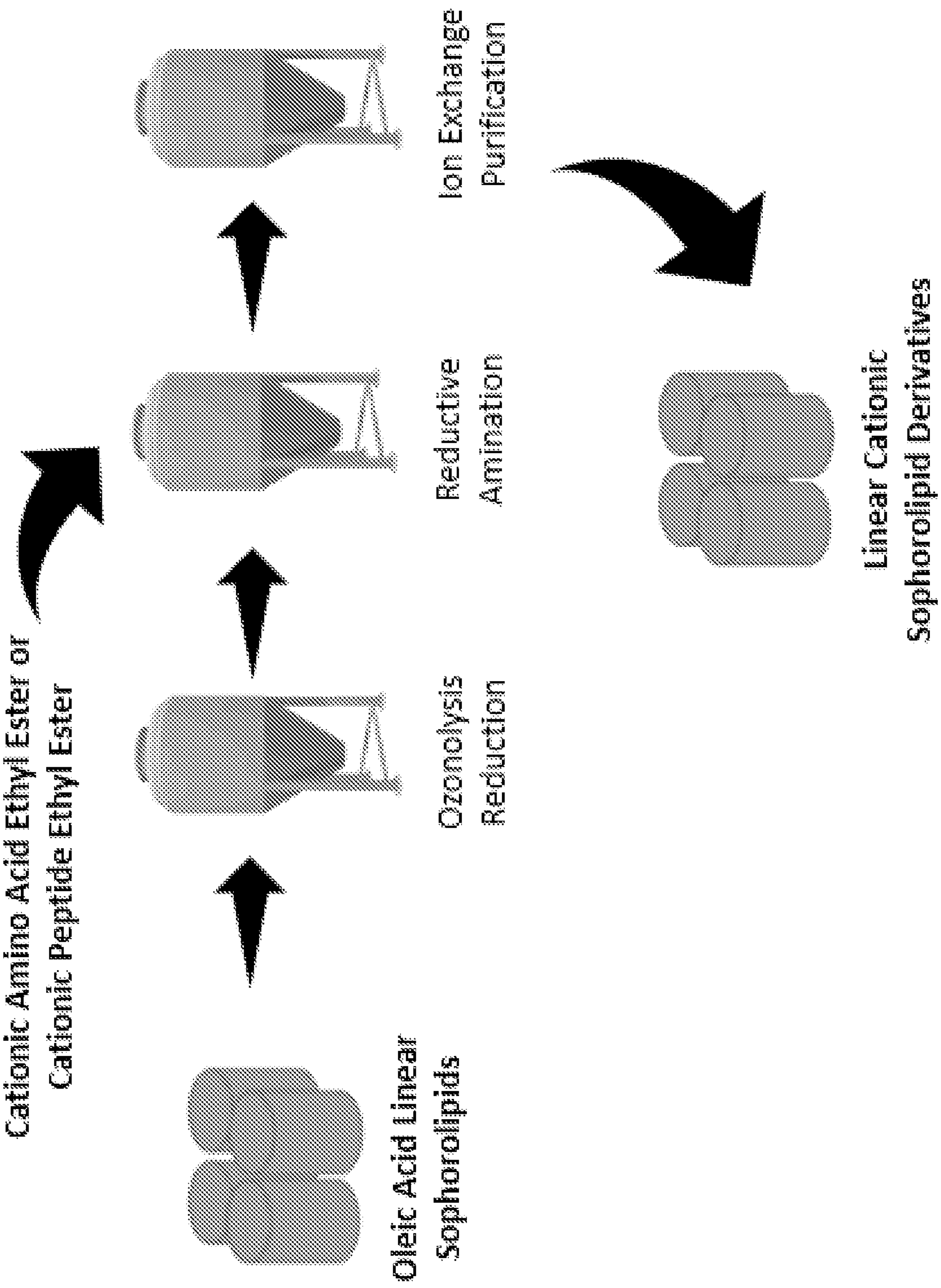
FIG. 3 depicts a production scheme according to an embodiment of the subject invention used to produce linear cationic sophorolipids.

After removal of spectator cations, a two-step synthetic scheme can be employed to generate a reactive aldehyde handle on the purified linear SLP—the first isolated intermediate of the subject methods—and then install naturally-derived cationic biodegradable functional groups. FIG. 3. Sophorolipids containing an unsaturated bond at a specific position allows for site-directed functionalization of the SLP molecule.

Step 1—Ozonolysis

In certain embodiments, the purified linear SLP are moved to a new clean vessel containing multiple air spargers with large surface area to undergo ozonolysis. During ozonolysis of the linear SLP, the olefin moiety of the SLP molecule is converted to an ozonide, a reactive 5-membered ring.

In a preferred embodiment, the purified linear SLP are ozonated with 2 to 3 vvm of 100% ozone gas for 2 to 20 hours, 3 to 16 hours, or 4 to 10 hours. The temperature is preferably at or about −78° C.

In one exemplary embodiment, the purified linear SLP are ozonated with 3 vvm of 100% ozone gas for 4 hours. In other exemplary embodiment, the purified linear SLP are ozonated with 2 vvm of 100% ozone gas for 16 hours.

Following ozonolysis, in certain embodiments, the SLP-ozonide is degassed with compressed air for 2 to 20 hours, 3 to 16 hours, or 4 to 10 hours at 2 to 3 vvm.

In one exemplary embodiment, the SLP-ozonide is degassed with compressed air for 4 hours at 3 vvm. In another exemplary embodiment, the SLP-ozonide is degassed for 16 hours at 2 vvm.

Figure 4:
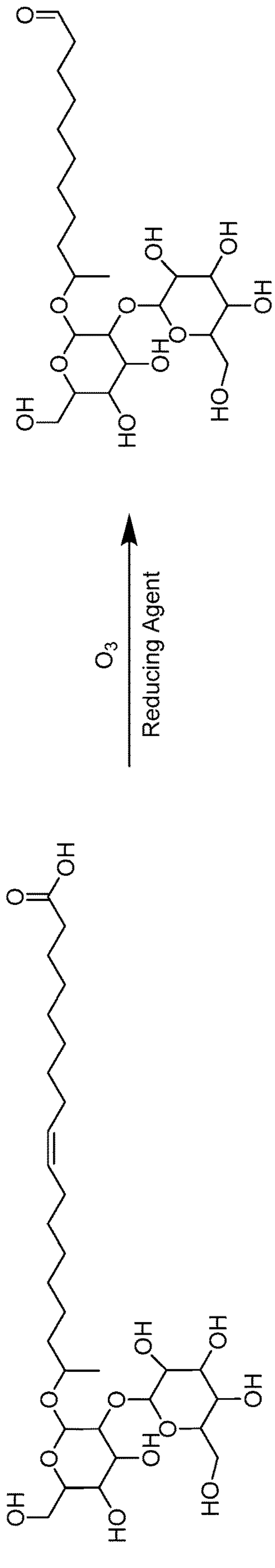
FIG. 4 depicts a reaction scheme according to an embodiment of the subject invention showing use of ozonolysis to produce a linear sophorolipid with an aldehyde at position 9.

In preferred embodiments, the SLP containing the ozonide is reduced to afford an aldehyde handle. FIG. 4. Following degassing, the SLP-ozonide is reacted with an inorganic reducing agent selected from, for example, triphenyl phosphine, sodium borohydride, magnesium sodium bisulfite and sodium metabisulphite. In a preferred embodiment, the reducing agent is triphenyl phosphine used in equimolar concentrations to the SLP-ozonide. Afterwards, the linear SLP aldehyde is preferably brought to room temperature.

Step 2—Reductive Amination

In preferred embodiments, step two of generating cationic SLP derivatives via the aldehyde handle comprises reductive amination of the linear SLP aldehyde.

Figure 5:
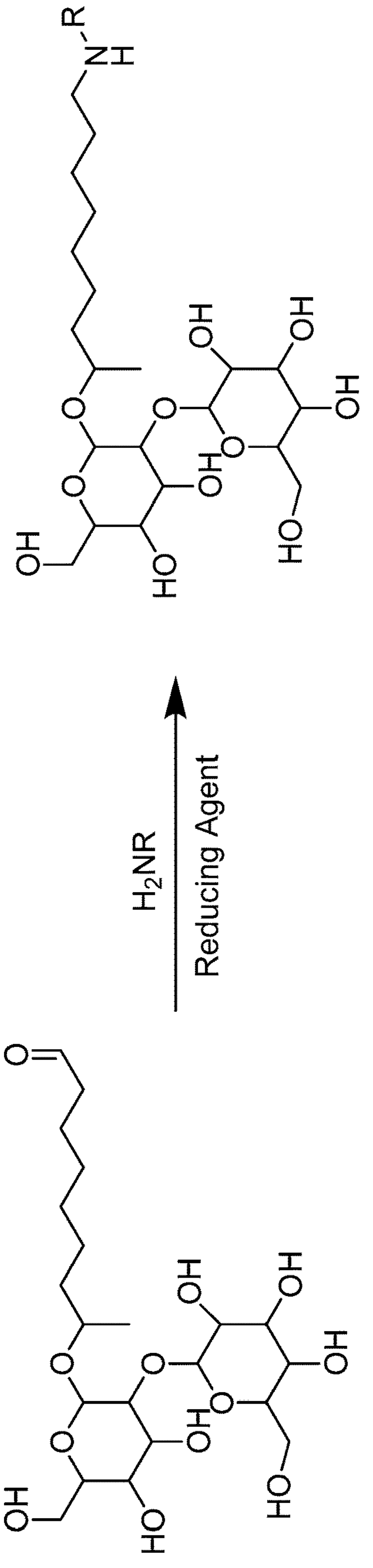
FIG. 5 depicts a reaction scheme according to an embodiment of the subject invention showing use of reductive amination to produce a linear sophorolipid. The R group can be any alkyl or aryl group containing one or more cationic amines derived from amino acids.

In certain embodiments, the reductive amination comprises introducing a primary amine to the aldehyde handle under reducing conditions. This produces a stable secondary amine that serves as a covalent linkage between the SLP “scaffold” and the “cargo” of the primary amine. FIG. 5.

First, in some embodiments, the linear SLP aldehyde is extracted with ethyl acetate from the aqueous mixture and concentrated and dried under reduced pressure (e.g., about 200 to 250 mbar, or about 240 mbar) at a temperature of about 35 to 45° C. The dried crude linear SLP aldehyde can then be dissolved in a reaction medium comprising tetrahydrofuran (THF) and/or water. The percentage of water used as the reaction medium preferably does not exceed 50% water, and typically is between 0 to 25%.

For the amination reaction, a primary amine is introduced to the extracted linear SLP aldehyde along with a reducing agent and a weak organic acid, preferably acetic acid, although other organic acids may be used (e.g., formic acid, trifluoracetic acid).

In certain embodiments, the primary amine is a cationic amino acid, such as, e.g., arginine, lysine or histidine. In certain embodiments, the primary amine is a short peptide containing repeats of cationic amino acids. In certain embodiments, the primary amine is a short peptide containing glycine residues as spacers, either between the SLP scaffold and the primary amine cargo, and/or between cationic amino acid residues.

In certain preferred embodiments, the primary amine is delivered via an amino acid ethyl ester and/or a peptide ethyl ester. In certain embodiments, the reducing agent is sodium cyanoborohydride, sodium triacetoxyborohydride or sodium borohydride.

In a preferred exemplary embodiment, the reaction utilizes an amino acid ethyl ester of arginine (Arg) with sodium triacetoxyborohydride as the reducing agent.

In another exemplary embodiment, the reaction utilizes an amino acid ethyl ester of histidine (His) or of lysine (Lys) with sodium triacetoxyborohydride as the reducing agent.

In further exemplary embodiments, the peptide ethyl esters are Arg-Arg-Arg-Arg, Gly-Gly-Arg-Arg, Gly-Arg-Gly-Arg, Gly-Arg-Arg-Arg or other combinations in which individual residues can be substituted from Arg, His, Lys, or glycine (Gly). FIGS. 8-12. In certain embodiments, the addition of glycine spacers enhances the water- and/or alcohol-solubility of the SLP derivative. In certain embodiments, the addition of glycine spacers enhances the antimicrobial activity of the SLP derivative by, for example, increasing the chain length of the fatty acid moiety. Advantageously, the chain length can be increased without requiring alteration of fermentation parameters during initial production of the linear SLP substrate.

Additional or Alternative Chemical Transformations to Obtain Linear Sophorolipid Containing an Aldehyde Functional Group and a Secondary Amine.

Figure 13:
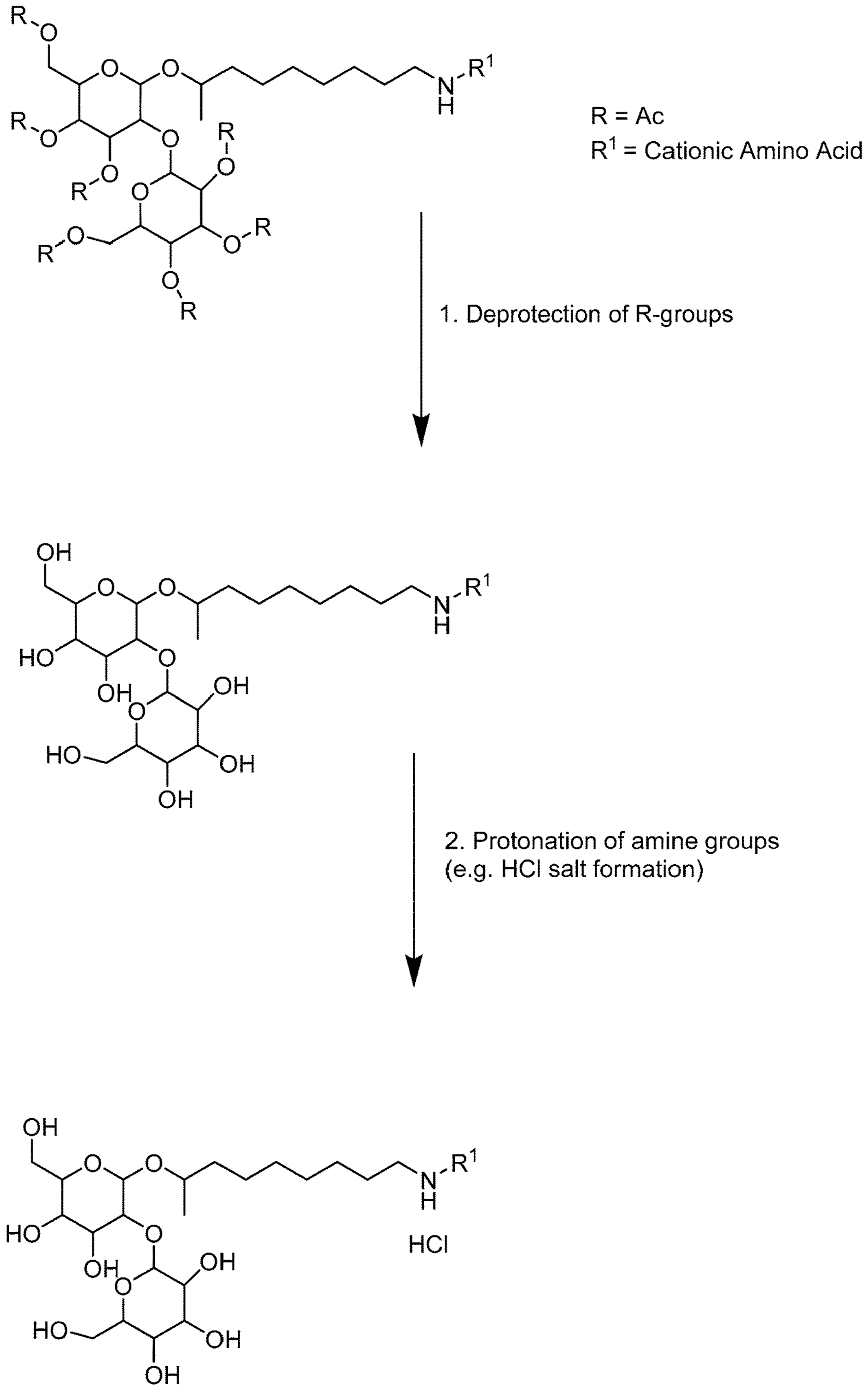
FIG. 13 depicts examples of a reaction scheme according to an embodiment of the subject invention showing removal of alcohol protecting groups and subsequent amine salt formation of sophorolipid derivatives.
Figure 14:
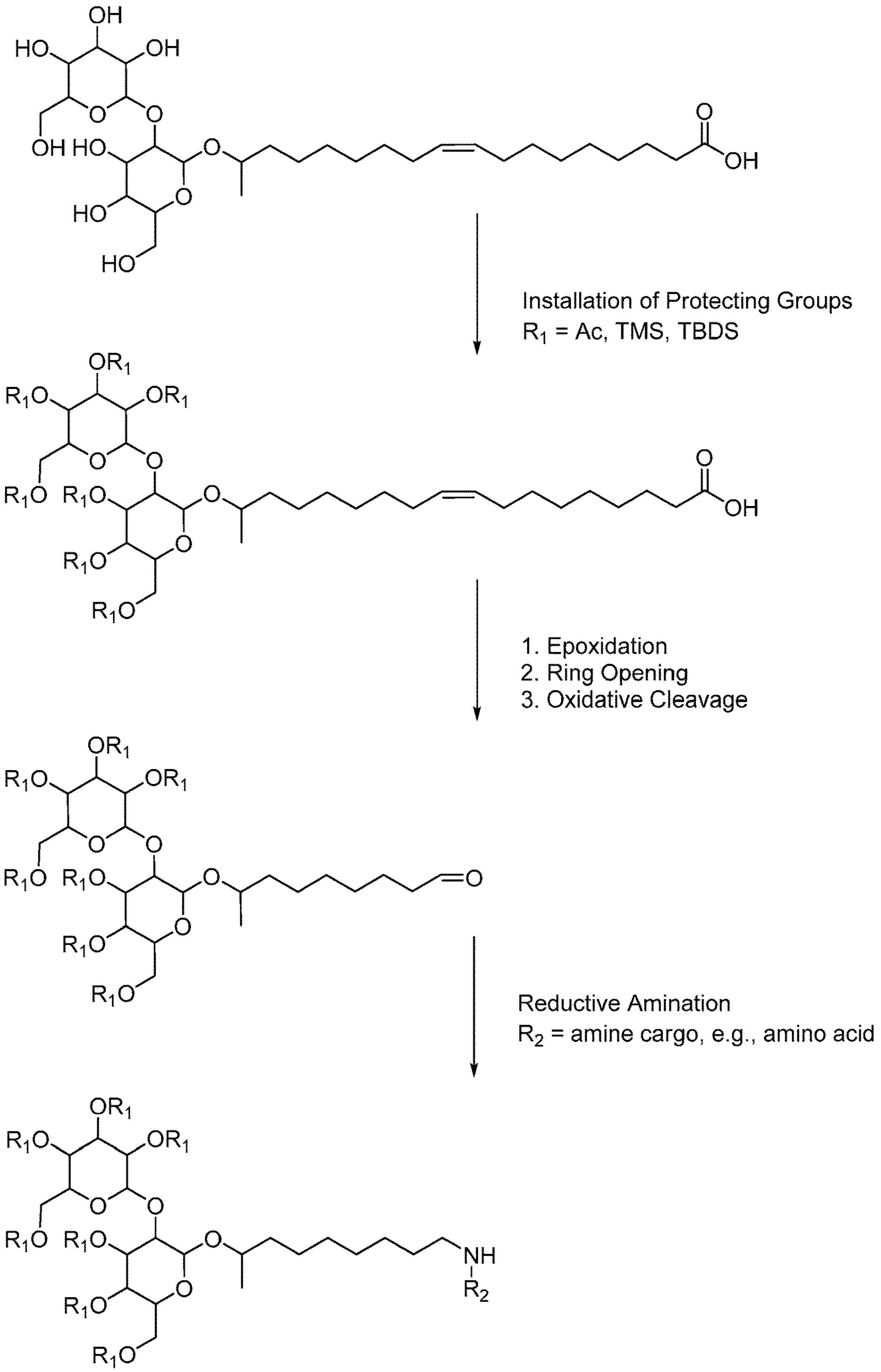
FIG. 14 depicts a reaction scheme according to an embodiment of the subject invention showing a three-step synthetic pathway to linear sophorolipid with a secondary amine, which does not require ozonolysis of the alkene functional group.

In certain embodiments, an alternative to the two-step method utilizing ozonolysis is employed to produce linear SLP aldehydes containing a secondary amine. FIGS. 13-14.

In certain embodiments, the hydrolyzed linear SLP substrate serves as the starting material. In some embodiments, protecting groups can be installed on every alcohol group of the SLP sophorose ring. Non-limiting examples of protecting groups include acetyl, trimethylsilyl ether, and tert-butyldiphenylsilyl ether, but many examples of alcohol protecting groups are well known to those skilled in the art.

In preferred embodiments, the alkene group of the SLP is transformed into an aldehyde moiety without the use of ozonolysis. Instead, the alkene is epoxidized to an oxirane ring using a peracid reagent (an example of the Prilezhaev reaction) or osmium tetroxide. Examples of a peracid reagent used according to the subject method include but are not limited to m-chloroperoxybenzoic acid, peroxyacetic acid, and performic acid.

The resulting epoxide ring is then opened into a vicinal diol. In certain embodiments, this is carried out under acid-catalyzed (aqueous) or base-catalyzed (aqueous) conditions.

Lastly, the vicinal diol is oxidatively cleaved to produce the aldehyde group. Oxidative cleavage of the vicinal diol can be accomplished by an appropriate oxidant such as, for example, sodium periodate.

After the oxidative cleavage of the vicinal diol, the protecting groups, if present, may be removed by traditional methods known for a specific group. For example, silyl ether protecting groups can be removed using an aqueous source of the fluoride ion such as tetrabutylammonium fluoride, since the very strong Si—F bond that forms between the silicon and fluorine atoms drives the deprotection reaction to completion.

After obtaining the linear sophorolipid containing an aldehyde, it can be transformed into the aforementioned derivatized species through the chemical transformations outlined earlier and in FIG. 4.

In certain embodiments, it is desirable to preserve the initial alkyl chain length while carrying out chemical transformations to obtain an aldehyde functional group. This can be achieved in several ways.

Figure 15:
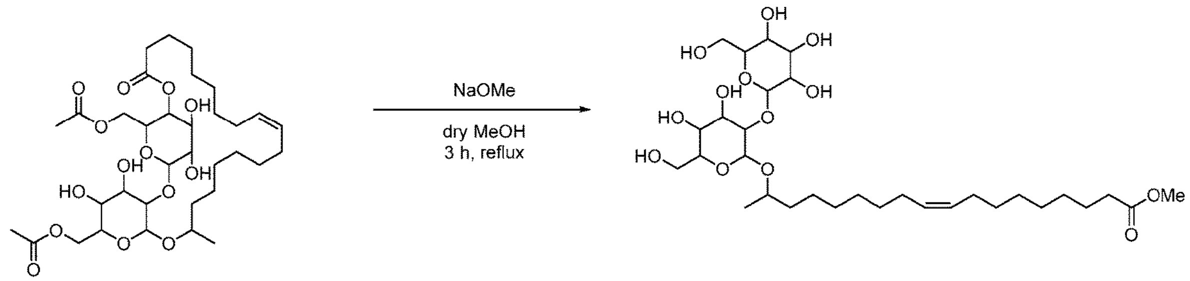
FIG. 15 depicts a reaction scheme according to an embodiment of the subject invention showing a synthetic route to linear sophorolipid containing aldehyde and alkene functional groups while retaining the original alkyl chain length.
Figure 15:
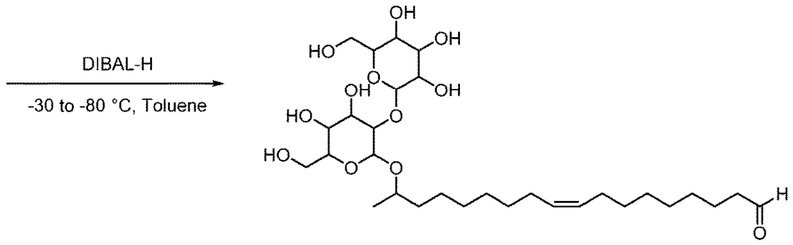

In one embodiment, a two-step synthetic route is employed using a lactonic SLP as the starting material. FIG. 15. Initially the lactonic SLP undergoes an alkaline hydrolysis to simultaneously remove acetyl groups while converting the free carboxylic acid group into a methyl ester. Using a reducing agent such as, for example, DIBAL-H, the methyl ester can be converted into an aldehyde functional group. After obtaining the linear sophorolipid containing an aldehyde, it can be transformed into the aforementioned derivatized species through the chemical transformations outlined earlier and in FIG. 4.

Figure 16:
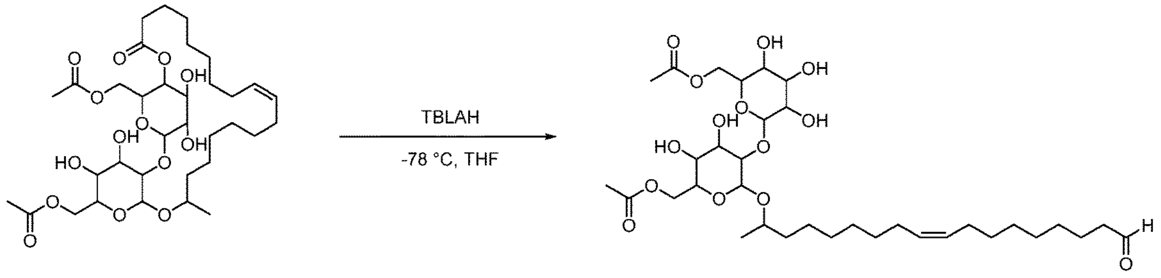
FIG. 16 depicts a reaction scheme according to an embodiment of the subject invention showing a direct reduction of a lactonic sophorolipid to the linear sophorolipid containing aldehyde and alkene functional groups while retaining the original C18 alkyl chain.

In another embodiment, the linear sophorolipid containing an aldehyde can be produced by a one-step, direct reduction of the lactone bond present in the lactonic SLP fermentation product. FIG. 16. Under certain conditions, for example, with the complex reducing agent formed between diisobutylaluminum hydride and tert-butyllithium (ate complex), the lactone bond can be directly reduced in one step to the aldehyde. Besides the ate complex, other examples of possible reducing agents include but are not limited to lithium tri-tertbutoxyaluminum hydride (TBLAH), lithium diisobutyl-tert-butoxyaluminum hydride (LDBBA), and diisobutylaluminum hydride and n-butyllithium ate complex. After obtaining the linear SLP containing an aldehyde, it can be transformed into the aforementioned derivatized species through the chemical transformations outlined earlier and in FIG. 4.

Figure 6:
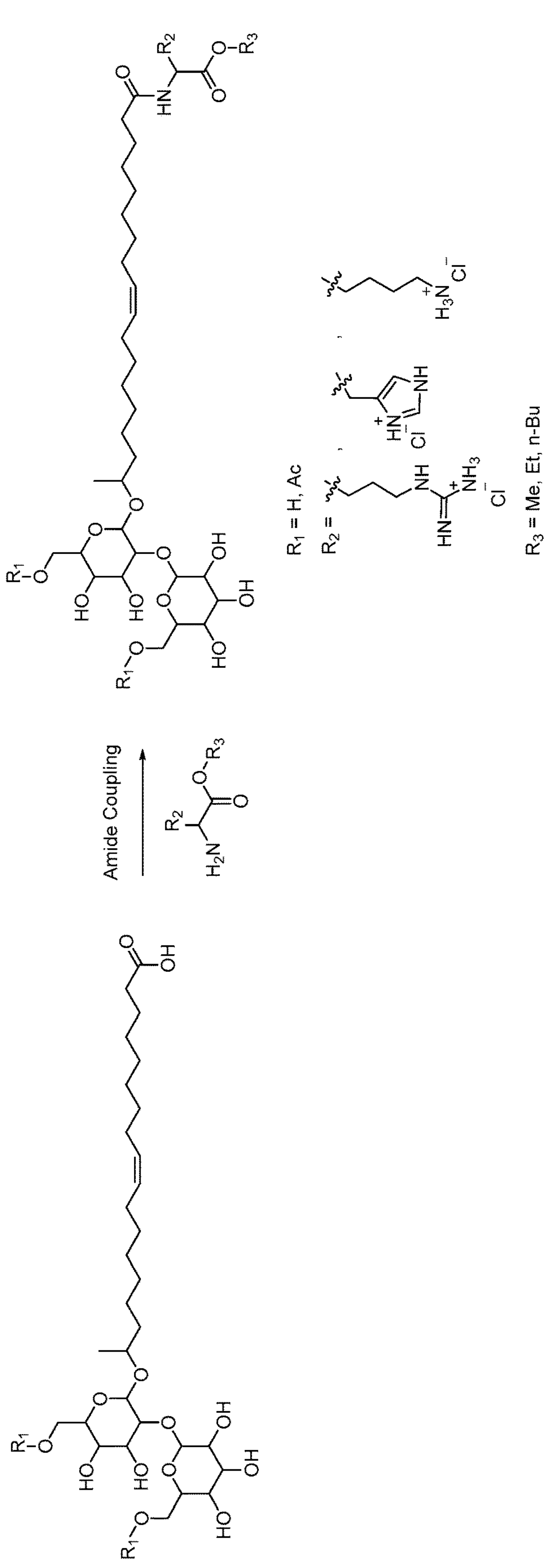
FIG. 6 depicts a reaction scheme according to an embodiment of the subject invention showing amide coupling of a linear SLP substrate to produce a long-chain amide containing a cationic amino acid residue.

Obtaining Derivatized SLP Containing a Short-Chain or Long-Chain Amide Functional Group In certain embodiments, the linear SLP substrate can be installed with an amide comprising cationic amino acid functional groups to produce a long-chain amide derivative (e.g., C18). FIG. 6.

Figure 7A:
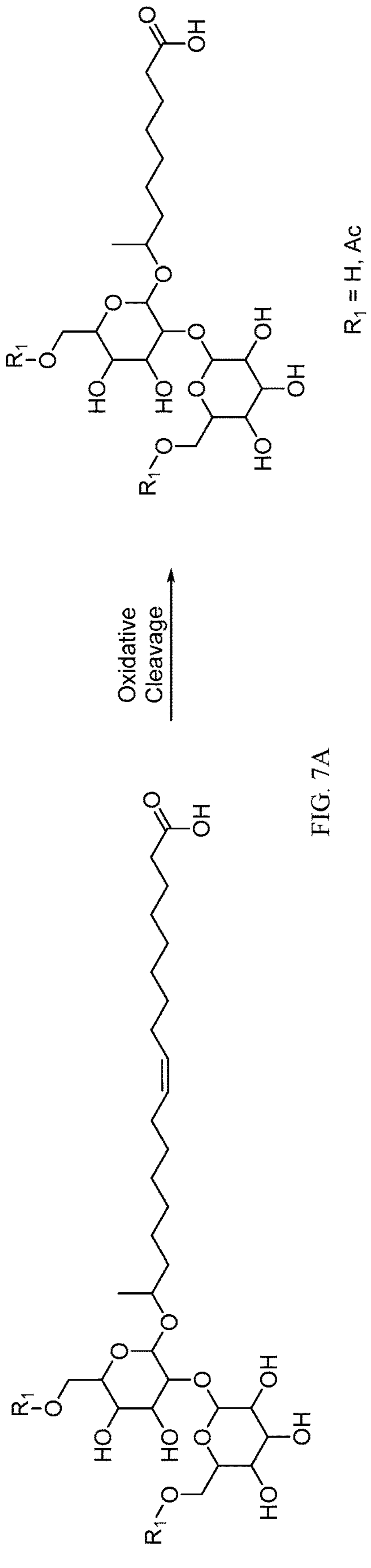
FIGS. 7A-7B depict (A) a reaction scheme according to an embodiment of the subject invention showing oxidative cleavage of a linear SLP substrate to produce a truncated acid, and (B) a reaction scheme according to an embodiment of the subject invention showing amide coupling of the truncated acid to produce a short-chain amide containing a cationic amino acid residue.
Figure 7B:
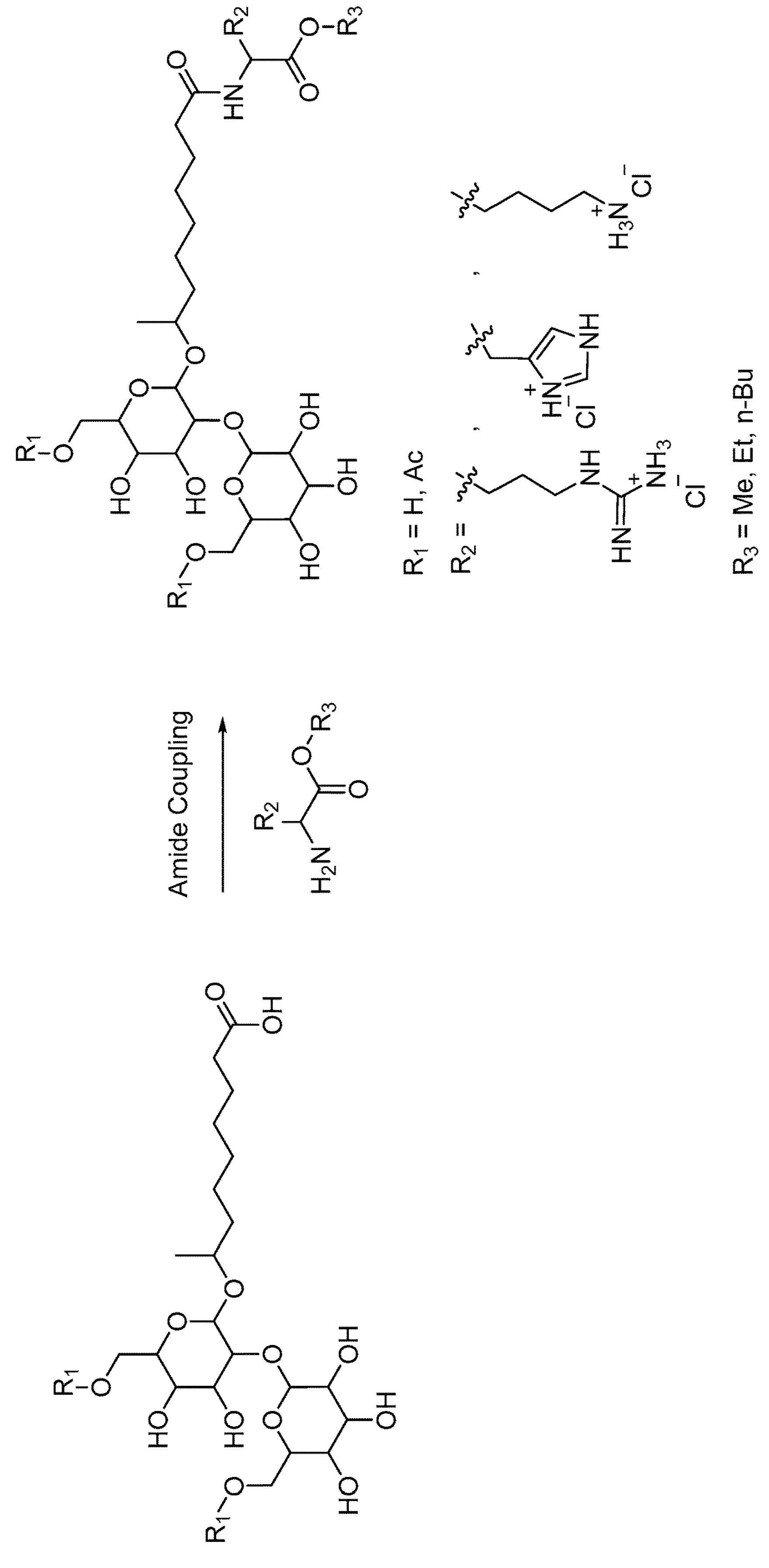
Figure 8A:
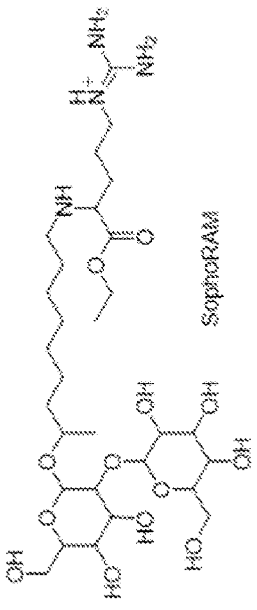
FIGS. 8A-8B depict examples of linear mono-cationic sophorolipid derivatives according to embodiments of the subject invention.
Figure 8A:
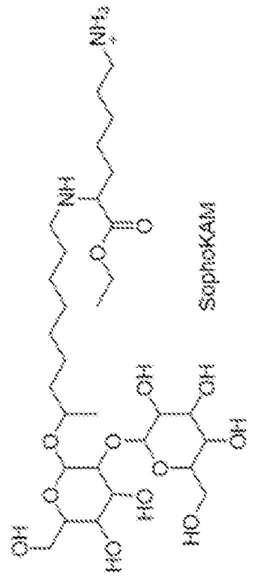
Figure 8A:
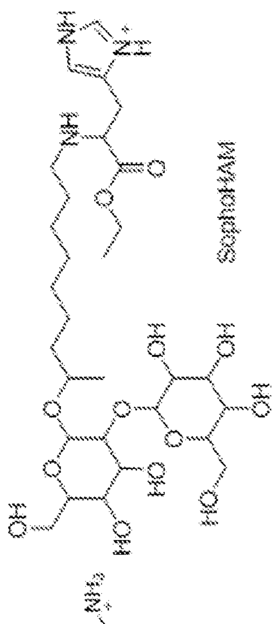
Figure 8A:
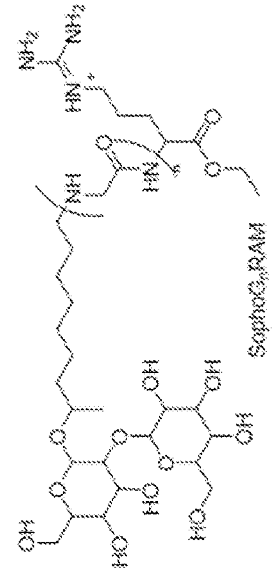
Figure 8A:
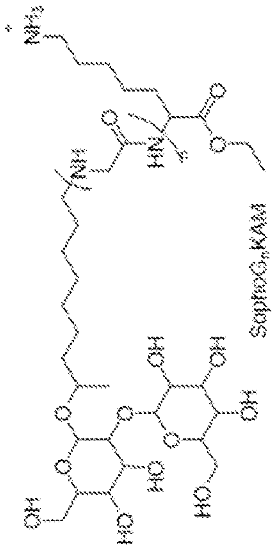
Figure 8A:
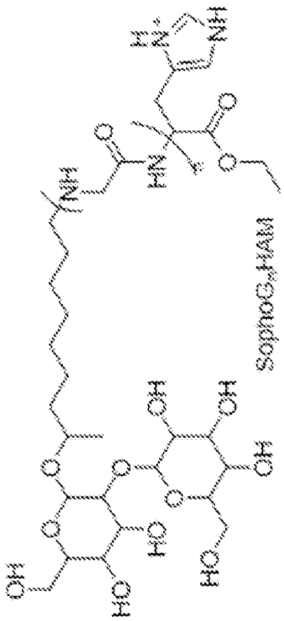
Figure 8B:
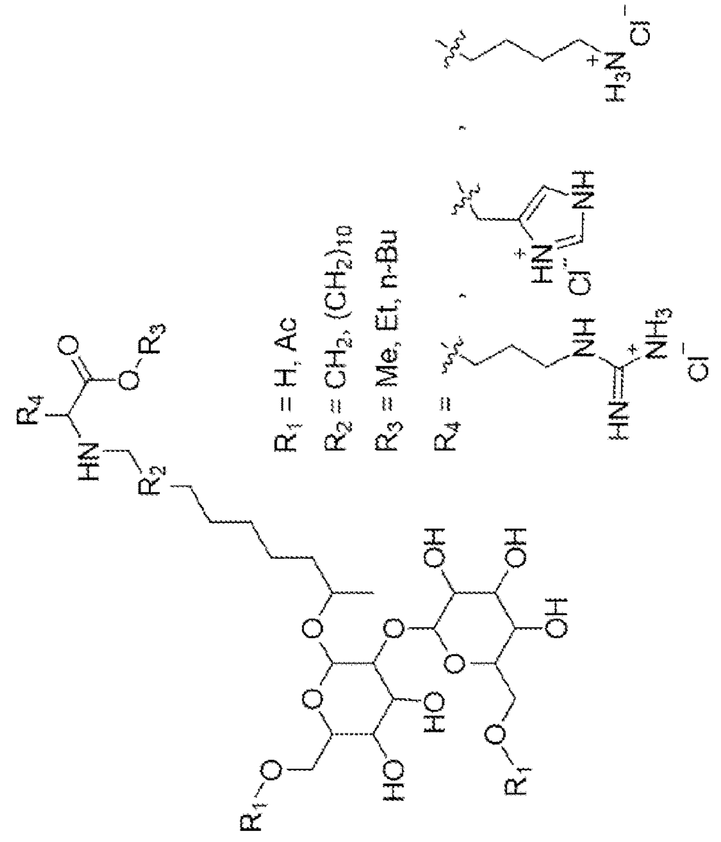
Figure 8B:
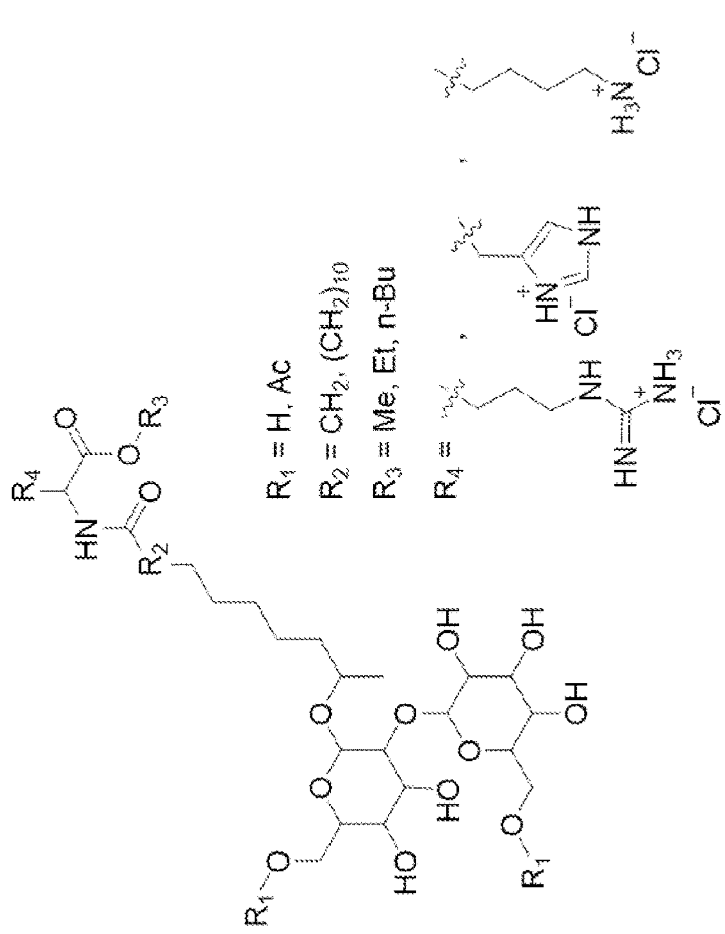
Figure 9:
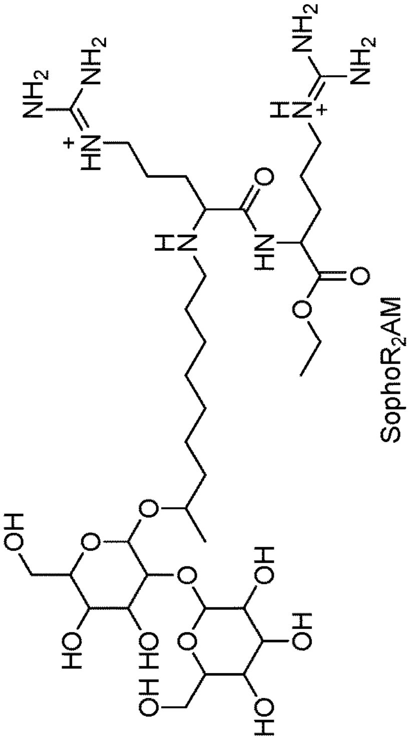
FIG. 9 depicts examples of linear poly-cationic sophorolipid derivatives according to embodiments of the subject invention. All amino acid residues are variable and can be substituted with, for example, arginine, glycine, histidine, and/or lysine
Figure 9:
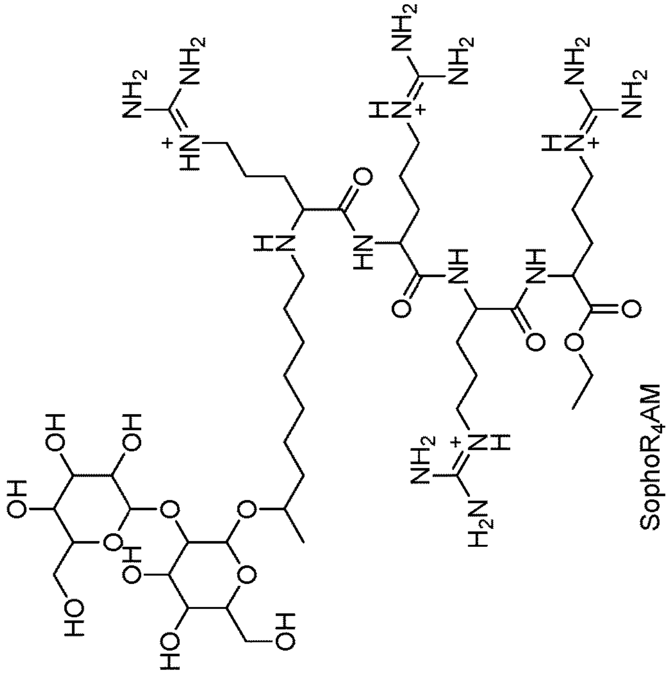
Figure 9:
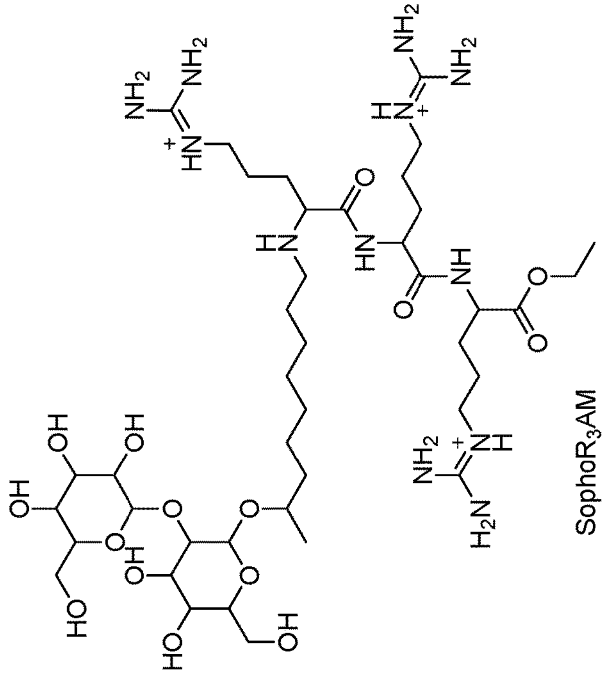
Figure 10:
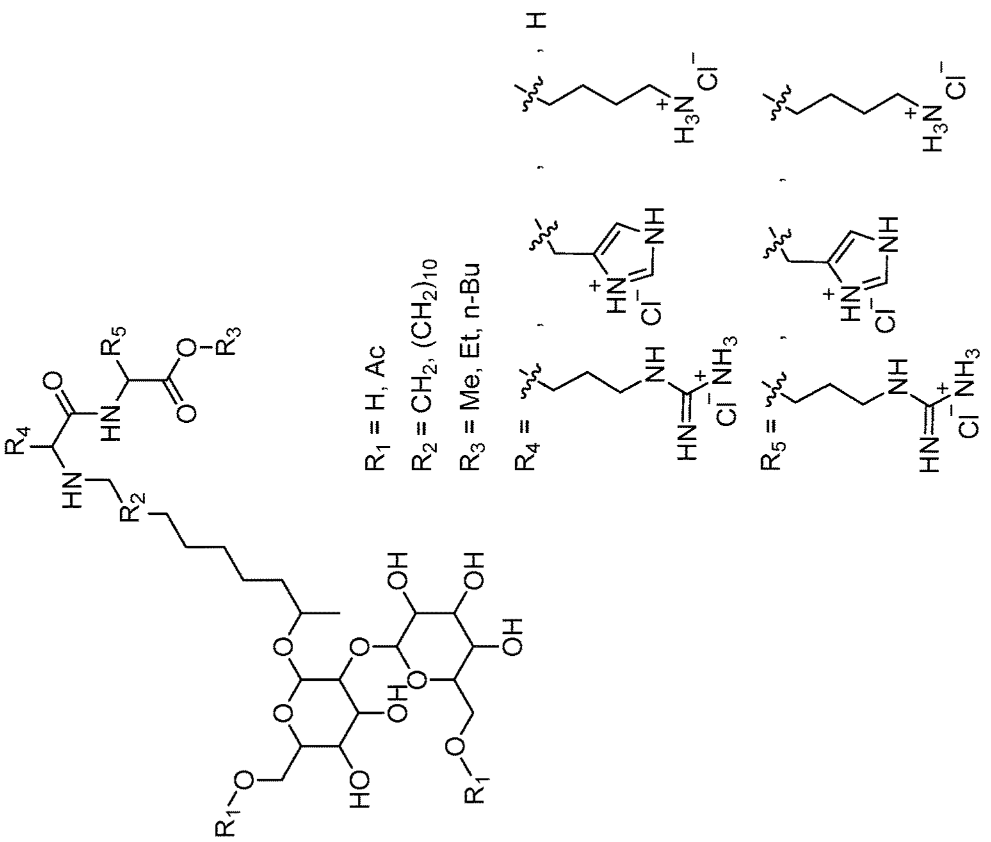
FIG. 10 depicts examples of up to di-cationic linear sophorolipid derivatives according to embodiments of the subject invention.
Figure 10:
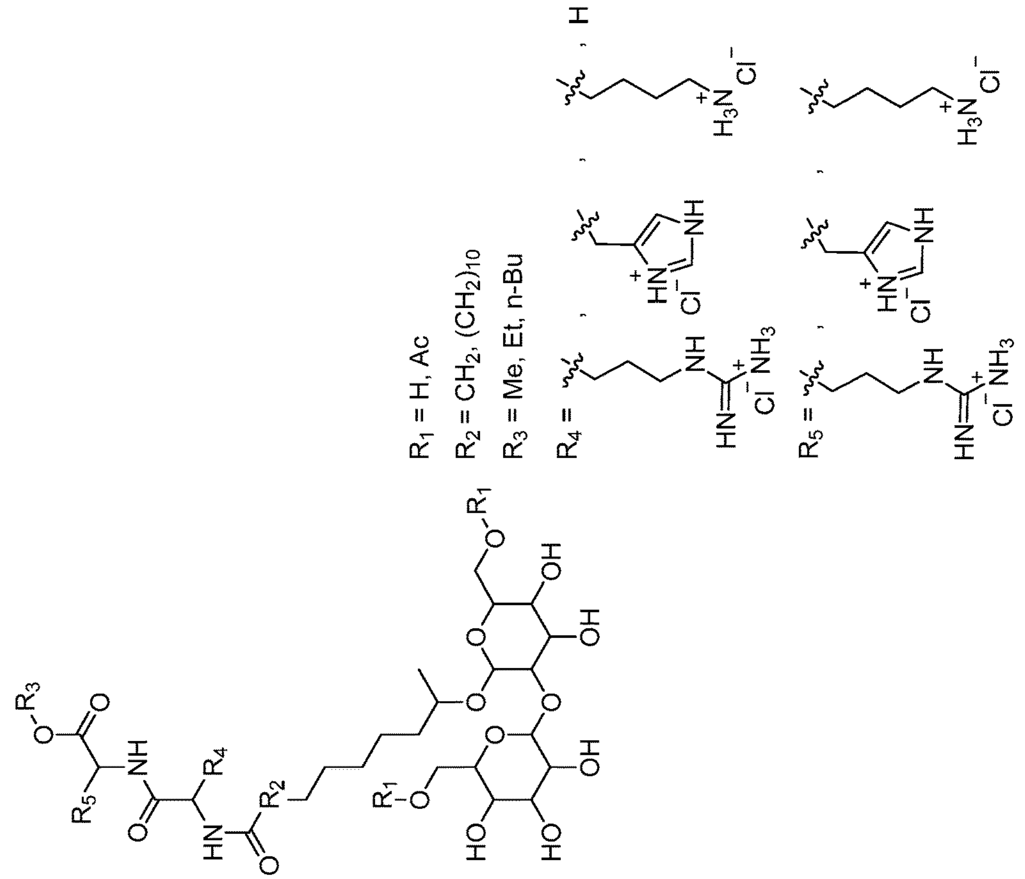
Figure 11:
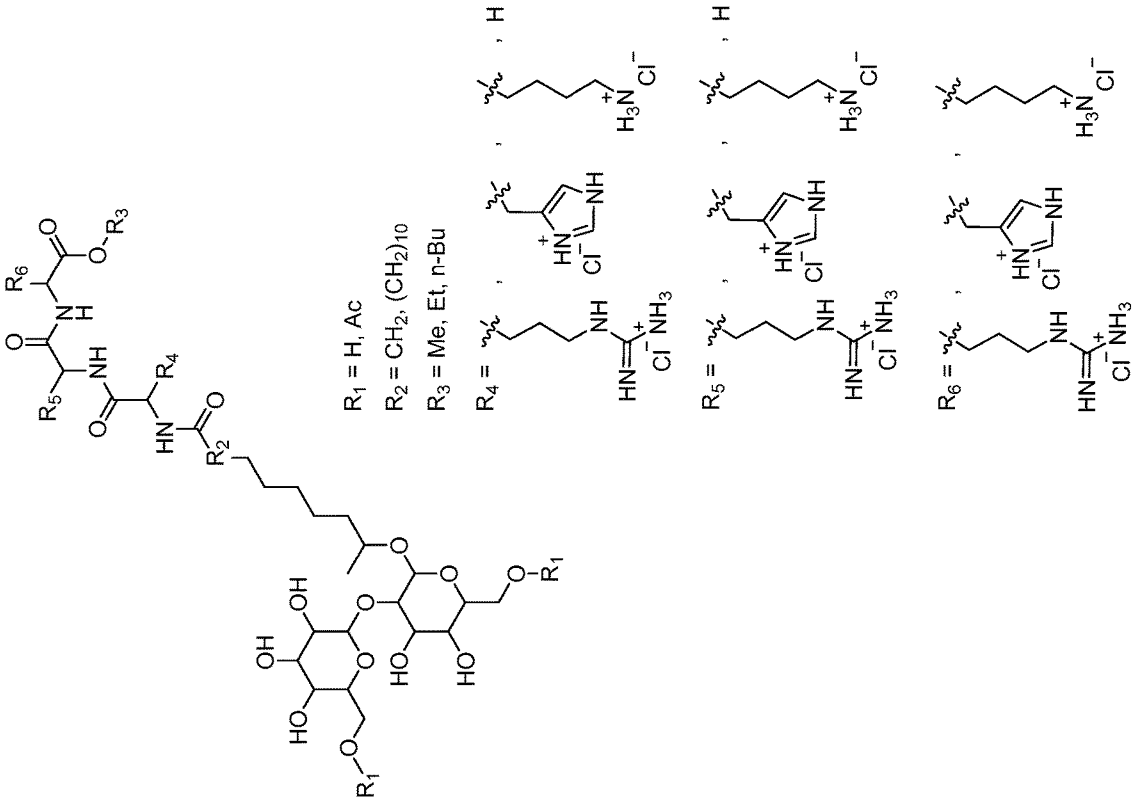
FIG. 11 depicts examples of up to tri-cationic linear sophorolipid derivatives according to embodiments of the subject invention.
Figure 11:
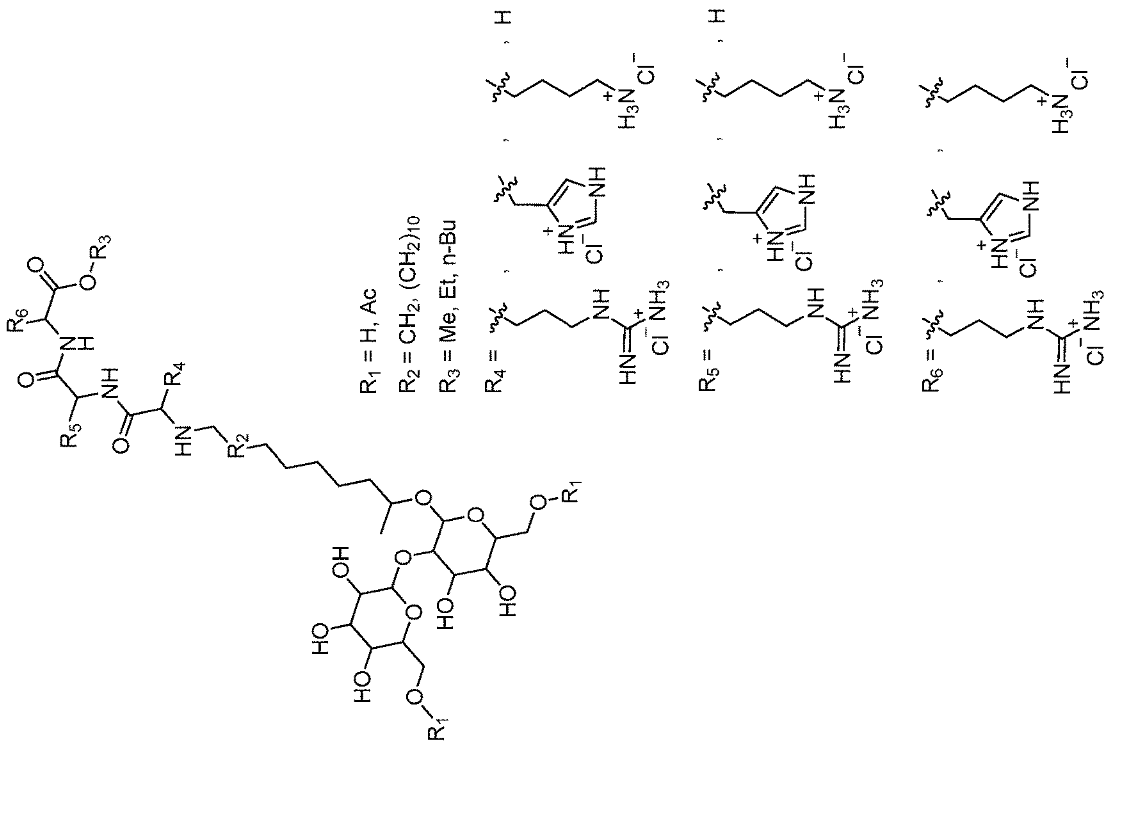
Figure 12:
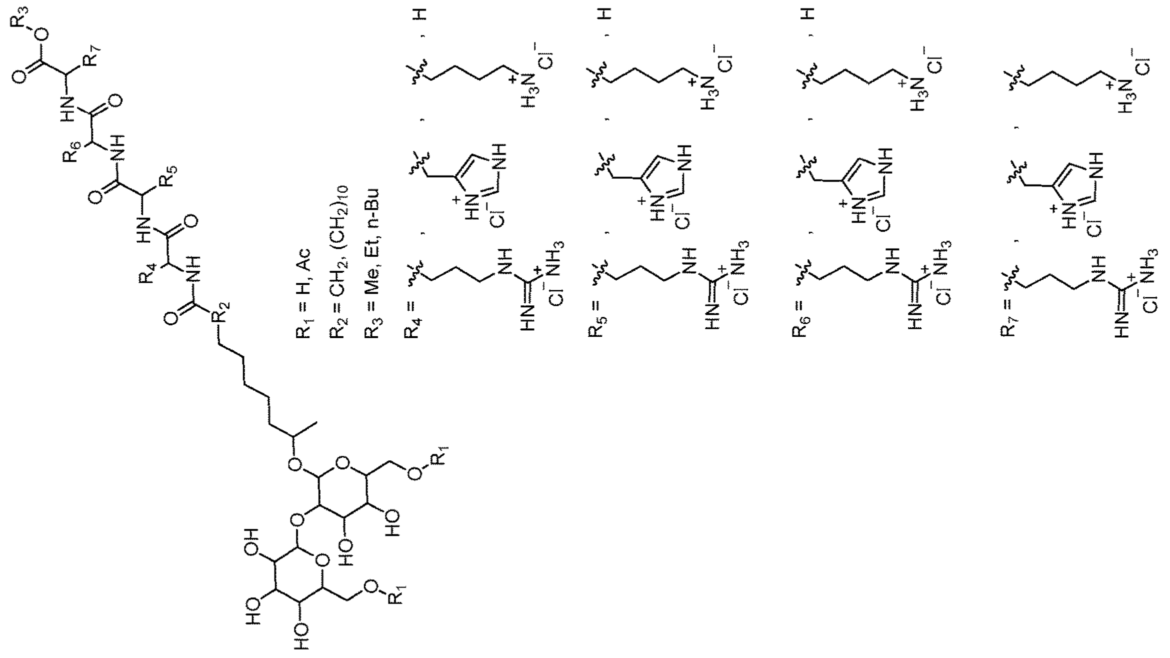
FIG. 12 depicts examples of up to tetra-cationic linear sophorolipid derivatives according to embodiments of the subject invention.
Figure 12:
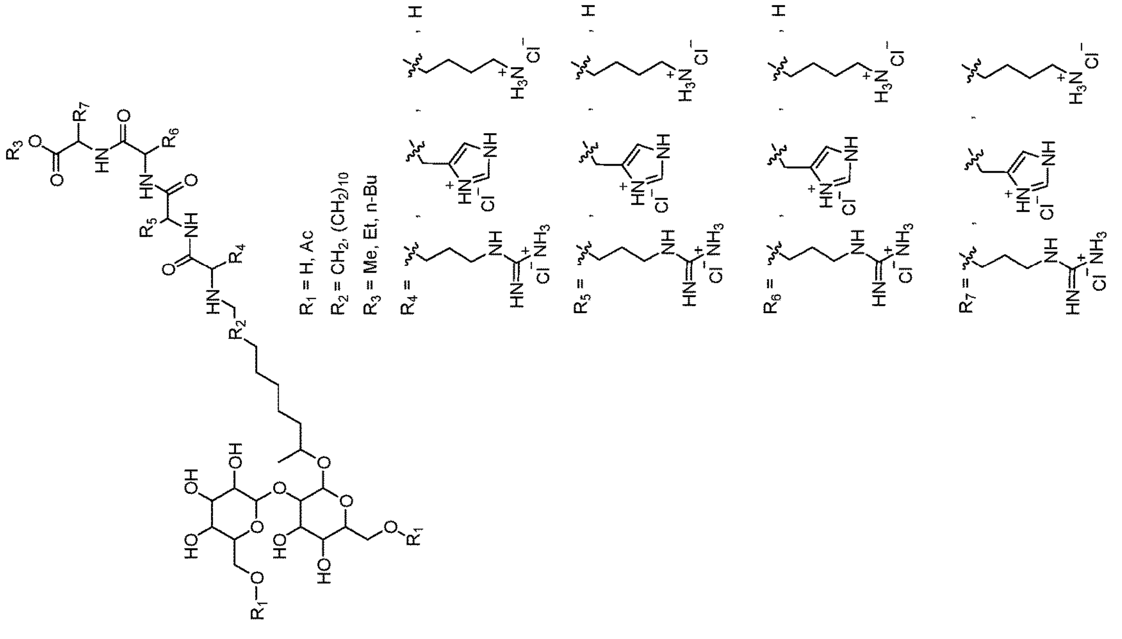

In some embodiments, the linear SLP substrate can be converted to a short-chain amide (e.g., C9) by first, truncating the fatty acid tail via oxidative cleavage, and second, installing an amide comprising cationic amino acid functional groups to the truncated acid. FIGS. 7A-7B.

Coupling agents for use in amide installation according to the subject invention can include, for example, 1-Ethyl-3-(3-dimethylaminopropyl)carbodiimide (EDCI/HOBt), Benzotriazol-1-yloxytripyrrolidinophosphonium hexafluorophosphate (PYBOP), 2-(1H-Benotriazole-1-yl)-1,1,3,3-tetramethylaminium tetrafluoroborate (TBTU), and/or N,N'-Dicyclohexylcarbodiimide/1-Hydroxybenzotriazole (DCC/HOBt). In certain embodiments, the preferred coupling agent is EDCI/HOBt.

In certain embodiments, the linear SLP comprising the aldehyde handle as described previously can be converted into a long-chain or short-chain amide utilizing similar reaction schemes. In some embodiments, the truncated acid (FIG. 7A) can serve as a substrate for installing the aldehyde handle described previously.

Ion Exchange/Purification

In certain embodiments, the unique cationic nature of the SLP derivatives of the subject invention allows for cationic ion exchange resins to be used for selective purification, e.g., selective retention of cationic species and/or selective removal of unreacted SLP and SLP that did not contain the desired carbon chain length or character. Thus, in certain embodiments, the subject invention provides novel methods of purifying SLP and SLP derivatives using cationic ion exchange resins.

In certain embodiments, following reductive amination, the cationic SLP derivative can be extracted from the reductive amination reaction mixture via a standard liquid-liquid extraction using an organic solvent, preferably ethyl acetate, washed with a pH 9.0 sodium carbonate buffer, and concentrated under reduced pressure (e.g., about 200 to 250 mbar, or about 240 mbar). The mixture can then be resuspended in deionized water and purified using cationic exchange resins.

In certain embodiments, the extracted cationic SLP are circulated through an ion exchange bed containing equimolar to 1.5 molar amounts of cation exchange sites to the concentration of the crude linear cationic SLP with, for example, a peristaltic pump or other type of pump, for a period of 2 to 20 hours, 3 to 15 hours, or 4 to 12 hours.

In preferred embodiments, removal of the SLP cationic derivatives from the resin is accomplished by application of an electrolyte solution containing a large concentration of monovalent metallic cations, wherein the large concentration is 1.5 to 15 molar equivalents, or 2 to 10 molar equivalents to the concentration of the SLP cationic derivatives. The monovalent metallic cations in large concentration outcompete the bound SLP cationic derivatives, allowing for them to exchange on the resin and produce a highly purified stream of SLP cationic derivatives.

In some embodiments, following reductive amination, the cationic SLP derivative can be purified by stirring it with saturated ammonium chloride solution to produce a stirred mixture; extracting the cationic SLP derivative by applying $CH_2Cl_2$ solvent (3×) to the stirred mixture to produce an extraction mixture; removing trace water from the extraction mixture by applying $MgSO_4$ or $Na_2SO_4$; drying the extraction mixture under elevated pressure (e.g., 350 to 450 mbar, or 400 mbar) and at 35 to 45° C. to remove the $CH_2Cl_2$ solvent; and, applying 21% NaOEt/EtOH solution, $NaHCO_3$ or $KHCO_3$ base in ethanol to remove acetyl R groups from the cationic SLP derivative. The de-acetylated linear cationic SLP derivative can then be converted to an HCl salt via reaction with a 1.25M HCl/EtOH solution.

Cleaning Composition

In certain embodiments, the subject invention provides derivatized SLP molecules as described above and in the Figures.

In some embodiments, the derivatized cationic SLP produced according to the subject methods can be used as active ingredients in environmentally-friendly, or "green," cleaning compositions for efficiently disinfecting and/or sanitizing materials and/or surfaces contaminated with, for example, bacteria, viruses, fungi, molds, mildew, protozoa, biofilms, and/or other infectious organisms. Advantageously, in preferred embodiments, the compositions and methods are at least as effective for disinfecting materials and/or surfaces as antimicrobial peptides (AMPs), or cationic host defense peptides, as well as other chemical and/or synthetic cleaning formulations, such as QACs and SCAs.

The cleaning compositions can be formulated as, for example, liquids, microemulsions, dissolvable powders and/or granules, pressed powders, loose powders, diluted sprays, concentrates, aerosols, foams, encapsulated dissolvable pods, gels, and/or as a pre-moistened or water-activated cloth, sponge, wipe or other substrate. The cleaning compositions can be used as, for example, toilet bowl cleaners, laundry detergents, dishwashing detergents, hard and soft surface cleaners, water cleaners and/or air cleaners.

In some embodiments, the derivatized cationic SLP produced according to the subject methods can be used as active ingredients in consumer products, serving as preservatives to prevent spoilage and/or growth of deleterious organisms, such as, for example, bacteria, viruses, fungi, molds, mildew, protozoa, biofilms and/or other infectious organisms. Such consumer products can include, for example, cleaning products (e.g., disinfectants, all-purpose cleaners, glass cleaners, laundry and dish detergents), home care products (e.g., floor polish, air fresheners), personal care products (e.g., skin care products, hair care products), cosmetics (e.g., makeup, nail polish), painting and building supplies (e.g., paints, lacquers, primers, putty, drywall, caulk), and in some embodiments, health, food and beverage products.

Advantageously, the present invention can be used without causing harm to users and without releasing large quantities of polluting and toxic compounds into the environment. Additionally, the compositions and methods utilize components that are biodegradable and toxicologically safe. Thus, the present invention can be used in a variety of industries as a "green" disinfectant.

In certain embodiments, the cleaning composition comprises the cationic derivatized SLP at 0.1 to 10% by weight, 0.1 to 9.0%, 0.1 to 8.0%, 0.1 to 7.0%, 0.1 to 6.0%, 0.1 to 5.0%, 0.1 to 4.0%, 0.1 to 3.0%, 0.1 to 2.0%, 1.0 to 9.0%, 1.0 to 5.0%, 1.0 to 3.0%, 3.0 to 10%, 3.0 to 7.0%, 5.0 to 10%, 5.0 to 9.0%, 6.0 to 10%, 7.0 to 10% and 8.0 to 10%. In certain embodiments, the cationic derivatized SLP is present in the composition at about 1 ppm to about 200 ppm, or about 2 ppm to about 250 ppm, or about 5 ppm to about 300 ppm, or about 10 ppm to about 350 ppm, or about 25 ppm to about 400 ppm, or about 50 ppm to about 450 ppm, or about 75 ppm to about 500 ppm, or about 100 ppm to about 600 ppm, or about 125 ppm to about 750 ppm, or about 150 ppm to about 1,000 ppm.

In a specific embodiment, the cationic derivatized SLP is present at a concentration of 50 to 500 ppm of the cleaning composition.

In certain embodiments, the SLP molecules according to the subject invention have advantageous micelle sizes. For example, in some embodiments, a sophorolipid molecule will form a micelle less than 500 nm, less than 100 nm, less than 50 nm, less than 25 nm, less than 15 nm or less than 10 nm in size. The size and amphiphilic properties of the micelle allow for enhanced penetration into pores so that greater contact can be made with impurities therein.

In certain embodiments, the pH of the cleaning composition ranges from 2.0 to 11.0, 2.5 to 10, 3.0 to 9.0, 3.0 to 8.0 or, preferably, 4.0 to 7.0. In certain embodiments, monocationic SLP derivatives are most stable at a pH between 3.0 to 7.0. In certain other embodiments, polycationic SLP derivatives are most stable at a pH between 3.0 and 8.0. Known pH adjusters can be utilized in order to keep the pH at a suitable level, including, for example, acetic acid, lactic acid and/or citric acid.

Optionally, the cleaning composition can further comprise one or more other components, including, for example, carriers (e.g., water), other biosurfactants, other surfactants (e.g., polyalkyglucosides such as capryl glucoside and lauryl glucoside, amine oxides), hydrophilic and/or hydrophobic syndetics, sequestrants, builders (e.g., potassium carbonate, sodium hydroxide, glycerin, citric acid, lactic acid), solvents (e.g., water, ethanol, methanol, isopropanol), organic and/or inorganic acids (e.g., lactic acid, citric acid, acetic acid, boric acid), essential oils, botanical extracts, cross-linking agents, chelators (e.g., potassium citrate, sodium citrate, sodium gluconate, citric acid), fatty acids, alcohols, reducing agents, oxidants, calcium salts, carbonate salts, buffers, enzymes, dyes, colorants, fragrances (e.g., d-limonene, thymol, citral, lavender), preservatives (e.g., octylisothiazolinone, methylisothiazolinone), terpenes (e.g., d-limonene), sesquiterpenoids, terpenoids, emulsifiers, demulsifiers, foaming agents, defoamers, bleaching agents, polymers, thickeners and/or viscosifiers (e.g., xanthan gum, guar gum).

In an exemplary embodiment, the cleaning composition can comprise a cationic SLP derivative according to the subject invention formulated or delivered as a solution (1-50%) in a glycol solvent, such as, for example, glycerol, propylene, and/or butylene glycol. In certain embodiments, this exemplary formulation or delivery can further comprise up to 5% relative to the active antimicrobial of one or more acids such as, for example, acetic acid, lactic acid and/or citric acid.

In some embodiments, the composition comprises additional and/or other biosurfactants. Additional biosurfactants according to the subject invention can include, for example, glycolipids, lipopeptides, flavolipids, phospholipids, fatty acid esters, and high-molecular-weight biopolymers such as lipoproteins, lipopolysaccharide-protein complexes, and/or polysaccharide-protein-fatty acid complexes.

In one embodiment, the additional and/or other biosurfactant is a glycolipid, such as, for example, rhamnolipids (RLP), cellobiose lipids, trehalose lipids and/or mannosylerythritol lipids (MEL). Natural (or non-derivatized) SLP can also be used. In one embodiment, the biosurfactant is a lipopeptide, such as, for example, surfactin, iturin, fengycin, arthrofactin, amphisin, viscosin, lichenysin, paenibacterin, polymyxin and/or battacin, In one embodiment, the biosurfactant is another type of amphiphilic molecule, such as, for example, esterified fatty acids, saponins, cardiolipins, pullulan, emulsan, lipomanan, alasan, and/or liposan.

In one embodiment, the biosurfactant is a biosurfactant alcohol ester, such as, for example, a lactonic sophorolipid ethyl ester, a lactonic sophorolipid methyl ester, a lactonic sophorolipid isopropyl ester, a lactonic sophorolipid butyl ester, a linear sophorolipid ethyl ester, a linear sophorolipid methyl ester, a linear sophorolipid isopropyl ester, or a linear sophorolipid butyl ester.

In one embodiment, the biosurfactant is a metal-biosurfactant complex, wherein an antimicrobial metal, such as silver, is added to the biosurfactant molecule. In certain embodiments, the complex is a silver-sophorolipid complex.

In one embodiment, the biosurfactant is a mixture of lipopeptide biosurfactants (e.g., surfactin, iturin, fengycin and/or lichenysin) produced by, for example, *Bacillus amyloliquefaciens* NRRL B-67928 or *Bacillus subtilis* NRRL B-68031. In certain embodiments, the mixture of lipopeptides comprises >50% surfactin.

Methods for Disinfecting and/or Sanitizing Materials

In preferred embodiments, the subject invention provides methods for disinfecting and/or sanitizing materials (including fluids, such as air and/or water) and/or surfaces having a deleterious microorganism therein or thereon, wherein the method comprises applying a cleaning composition produced according to the subject invention to the material and/or surface such that the composition is contacted with the deleterious microorganism. Advantageously, the methods are safe for use in household, commercial, and industrial settings and in the presence of humans, plants and animals.

Advantageously, the methods can be used to disinfect and/or sanitize a broad spectrum of deleterious microorganisms, including both Gram-negative and Gram-positive bacteria, biofilms, viruses, fungi, molds, protozoa, parasites, algae, as well as other infectious organisms, such as worms and nematodes. In certain specific embodiments, the methods can be used for disinfecting a material and/or surface having *E. coli, Staphylococcus* spp., *Salmonella* spp., *Campylobacter* spp., and/or *Clostridium* spp. thereon.

The cleaning composition can be applied to, for example, a countertop, desk, floor, toilet, clothing, textile, plastic dish, ceramic dish, sink, bathtub, toy, doorknob, carpet, rug, glass, window, medical devise or implant, or fluid (e.g., air or water).

The cleaning composition can be applied directly to the material and/or surface by spraying using, for example, a spray bottle or a pressurized spraying device, or otherwise pouring or squeezing the composition onto or into the material and/or surface from a vessel. The cleaning composition can also be applied using a sponge, cloth, wipe or brush, wherein the composition is rubbed, spread or brushed onto the material and/or surface. Furthermore, the cleaning composition can be applied via a laundry washing machine or a dishwasher. Even further, the cleaning composition can be applied as an aerosol.

The cleaning composition can be used independently from or in conjunction with an absorbent and/or adsorbent material. For instance, the cleaning composition can be formulated to be used in conjunction with a cleaning wipe, sponge (cellulose, synthetic, etc.), paper towel, napkin, cloth, towel, rag, mop head, squeegee, and/or other cleaning device that includes an absorbent and/or adsorbent material. The cleaning composition can be pre-loaded onto an absorbent and/or adsorbent material, post-absorbed and/or post adsorbed by a material during use, and/or be used separately from an absorbent and/or adsorbent material.

A cleaning wipe, upon which the improved cleaning composition can be loaded thereon, can be made of an absorbent/adsorbent material. Typically, the cleaning wipe has at least one layer of nonwoven material. Non-limiting examples of commercially available cleaning wipes that can be used include DuPont 8838, Dexter ZA, Dexter 10180, Dexter M10201, Dexter 8589, Ft. James 836, and Concert STD60LN. All of these cleaning wipes include a blend of polyester and wood pulp. Dexter M10201 also includes rayon, a wood pulp derivative. The loading ratio of the cleaning composition onto the cleaning wipe can be about 2-5:1, or about 3-4:1. The cleaning composition is loaded onto the cleaning wipe in any number of manufacturing methods. Typically, the cleaning wipe is soaked in the cleaning composition for a period of time until the desired amount of loading is achieved. The cleaning wipe loaded with the improved cleaning composition provides excellent cleaning with little or no streaking/filming.

In one embodiment, the cleaning composition is left to soak on or in the material and/or surface for a sufficient time to achieve disinfection and/or sanitization. For example, soaking can occur for 5 seconds to 10 minutes, or from 10 seconds to 5 minutes, or from 30 seconds to 2 minutes. Preferably, the minimum exposure time required is less than 60 seconds, more preferably less than 30 seconds, in order to achieve disinfection and/or sanitization.

In one embodiment, the cleaning composition can be applied using agitation. This can be mechanical, for example, in a laundry washing machine or dishwasher, or manually, for example, by scrubbing with a cloth, wipe, sponge or brush.

In one embodiment, the method further comprises the step of removing the cleaning composition and deleterious microorganism(s) from the material and/or surface. This can be achieved by, for example, rinsing or spraying water onto the surface, and/or rubbing or wiping the surface with a cloth, wipe, sponge or brush until the cleaning composition and microorganism(s) have been freed from the material and/or surface. Rinsing or spraying with water can be performed before, during and/or after rubbing or wiping the surface.

In some embodiments, methods for preventing spoilage or contamination of a consumer product are provided, wherein a derivatized SLP according to the subject invention is applied with/to, or formulated with, the consumer product as a preservative ingredient. The consumer product can be, for example, a cleaning product, home care product, personal care product, cosmetic, painting and/or building supplies, and in some embodiments, health, food and beverage product.

Target Microorganisms for Disinfecting and/or Preservation

Advantageously, the methods can be used to disinfect, sanitize and/or preserve from (i.e., prevent contamination by) a broad spectrum of deleterious organisms and/or microorganisms, including both Gram-negative and Gram-positive bacteria, biofilms, viruses, fungi, molds, mildews, protozoa, nematodes, parasites, algae, and/or other infectious organisms. For example, in certain specific embodiments, the methods can be used for disinfecting a material and/or surface having deleterious bacteria therein or thereon, such as, for example, strains of *Bacillus, Alicyclobacillus, Geobacillus, Lactobacillus, Proteus, Serratia, Klebsiella, Obesumbacterium, Campylobacter, Clostridrium, Corynebacteria, Erwinia, Salmonella, Staphylococcus, Shigella, Yersinia, Moraxella, Photobacterium, Thermoanaerobacterium, Desulfotomaculum, Pediococcus, Leuconostoc, Oenococcus, Acinetobacter, Leuconostoc, Psychrobacter, Pseudomonas, Alcaligenes, Serratia, Micrococcus, Mycobacterium, Flavobacterium, Proteus, Enterobacter, Streptococcus, Xanthomonas, Listeria, Shewanella, Escherichia, Enterococcus* and/or *Vibrio.*

Specific bacteria include, for example, *Clostridium perfringens, Clostridium botulinum, Clostridium difficile, Staphylococcus aureus* (including MRSA), *Streptococcus pharyngitis, Streptococcus pneumoniae, Bacillus cereus, Bacillus subtilis, Escherichia coli, Xanthomonas campestris, Listeria monocytogenes, Vibrio cholera, Vibrio parahaemolytics, Shewanella putrefaciens*, vancomycin-resistant Enterococci, *Mycobacterium tuberculosis, Mycobacterium bovis*, and/or *Acinetobacter baumanii.*

In certain embodiments, the cleaning composition can have disinfecting and/or sanitizing capabilities against viruses, such as, for example, rotaviruses, hepatitis A, B, and C, Coxsackievirus, Rhinovirus, the cold virus, the flu virus, herpes viruses, cytomegalovirus, and poliovirus;

fungi, such as, for example, *Zygosaccharomyces* spp., Debaryomyces *hansenii, Candida* spp., *Dekkera/Brettanomyces* spp., *Leptosphaerulina* chartarum, *Epicoccum nigrum, Wallemia sebi, Cryptococcus* spp., *Trichophyton rubrum, Trichophyton mentagrophytes, Epidermophyton floccosum;* molds, such as, for example, *Alternaria, Aspergillus, Byssochlamys, Botrytis, Cladosporium, Fusarium, Geotrichum, Manoscus, Monilia, Mortierella, Mucor, Neurospora, Oidium, Oosproa, Penicillium*; and parasites, such as, for example, tapeworms, helminths, nematodes, *Toxoplasma, Trichinella, Giardia lambila, Entamoeba histolytica*, and *Cryptospordium.*

We claim:

1. A method for producing a cationic sophorolipid (SLP) derivative, the method comprising a) producing a linear SLP molecule having an 18-carbon fatty acid moiety with a single unsaturated bond at the ninth carbon, and one of b), c), or d):

b) subjecting the linear SLP molecule of a) to ozonolysis to oxidize the fatty acid moiety to an ozonide, and reducing the SLP-ozonide with a reducing agent to produce an aqueous crude linear SLP aldehyde;

c) subjecting the linear SLP molecule of a) to a process comprising:

1) Epoxidizing the alkene group of the SLP;

2) Opening the epoxide to form a vicinal diol; and

3) Oxidatively cleaving the vicinal diol to produce an aqueous crude linear SLP aldehyde; or d) converting the free carboxylic acid group of the linear SLP molecule of a) into a methyl ester using alkaline hydrolysis, and applying DIBAL-H as a reducing agent to convert the methyl ester into an aldehyde functional group, thereby producing a crude linear SLP aldehyde; and e) after one of b), c), or d), extracting the linear SLP aldehyde from the aqueous crude linear SLP aldehyde and subjecting the extracted linear SLP aldehyde to reductive amination, thereby producing a SLP scaffold covalently linked to a primary amine, said linked SLP scaffold and primary amine comprising the cationic SLP derivative, wherein the cationic SLP derivative is present in a reductive amination reaction mixture, and purifying the cationic SLP derivative from the reductive amination mixture wherein the reductive amination of e) comprises introducing a peptide ethyl ester to the linear SLP aldehyde in the presence of a reducing agent and weak organic acid, and wherein the peptide ethyl ester comprises Arg-Arg-Arg-Arg, Gly-Gly-Arg-Arg, Gly-Arg-Gly-Arg, or Gly-Arg-Arg-Arg.

2. The method of claim 1, wherein a) comprises cultivating a SLP-producing yeast in a fermentation medium comprising dextrose and a source of oleic acid for 48 to 120 hours at a dissolved oxygen level of 50 mM to 70 mM per liter per hour to produce a yeast culture product, said yeast culture product comprising fermentation broth, yeast cells and crude SLP, said crude SLP comprising a mixture of two or more SLP molecular structures, and subjecting the crude SLP to alkaline hydrolysis.

3. The method of claim 2, wherein the crude SLP comprises lactonic SLP, wherein the alkaline hydrolysis converts the lactonic SLP into crude linear SLP, and wherein a portion of, or all, of the crude linear SLP comprise one or more acetyl R groups.

4. The method of claim 2, wherein after the alkaline hydrolysis, the crude linear SLP are purified using an ion exchange resin, wherein the crude linear SLP are circulated through an ion exchange bed containing ion exchange sites for a period of time from 30 minutes to 3 hours, and wherein the amount of ion exchange sites is equimolar or up to 1.5 molar to the concentration of hydroxide salts utilized in the hydrolysis reaction.

5. The method of claim 1, wherein the ozonolysis of b) comprises ozonating the purified linear SLP with 3 vvm of 100% ozone gas for 4 to 16 hours at −78° C.

6. The method of claim 1, wherein the reducing agent of b) is selected from triphenyl phosphine, sodium borohydride, magnesium, sodium bisulfite, and sodium metabisulfite.

7. The method of claim 1, wherein the alkene is epoxidized in cl) using osmium tetroxide or a peracid reagent.

8. The method of claim 1, wherein extracting the linear SLP aldehyde from the aqueous crude linear SLP aldehyde in e) comprises mixing the aqueous crude linear SLP aldehyde with ethyl acetate, drying and concentrating the linear SLP with ethyl acetate at a pressure of 200 to 250 mbar and a temperature of about 35 to 45° C., and resuspending the dried linear SLP aldehyde in a mixture of tetrahydrofuran (THF) and/or water.

9. The method of claim 1, wherein purifying the cationic SLP derivative in e) comprises stirring the reductive amination reaction mixture comprising the cationic SLP derivative with saturated ammonium chloride solution to produce a stirred mixture;

extracting the cationic SLP derivative by applying $CH_2Cl_2$ solvent (3×) to the stirred mixture to produce an extraction mixture;

removing trace water from the extraction mixture by applying $MgSO_4$ or $Na_2SO_4$;

drying the extraction mixture at 400 mbar pressure at 35 to 45° C. to remove the $CH_2Cl_2$ solvent;

applying 21% NaOEt/EtOH solution, $NaHCO_3$ or $KHCO_3$ base in ethanol to the solvent-free cationic SLP derivative to remove acetyl R groups from the cationic SLP derivative; and converting the de-acetylated linear cationic SLP derivative to an HCl salt via reaction with a 1.25M HCl/EtOH solution.

* * * * *